US006339184B1

(12) United States Patent
Smith

(10) Patent No.: US 6,339,184 B1
(45) Date of Patent: Jan. 15, 2002

(54) AHAS INHIBITING HERBICIDE RESISTANT WHEAT AND METHOD FOR SELECTION THEREOF

(75) Inventor: Wendy A. Smith, Levittown, PA (US)

(73) Assignee: BASF Aktiengellschaft, Ludwigshafen (DE)

( * ) Notice: Subject to any disclaimer, the term of this patent is extended or adjusted under 35 U.S.C. 154(b) by 0 days.

(21) Appl. No.: 08/218,009

(22) Filed: Mar. 25, 1994

Related U.S. Application Data

(63) Continuation of application No. 07/681,831, filed on Apr. 8, 1991, now abandoned.

(51) Int. Cl.$^7$ ................................................ A01H 5/00
(52) U.S. Cl. ...................................... 800/276; 800/300
(58) Field of Search ........................ 800/235, DIG. 58, 800/298, 276, 268, 300; 47/58; 435/172.1, 172.3, 183; 504/214, 215, 247, 253

(56) References Cited

U.S. PATENT DOCUMENTS

| | | | |
|---|---|---|---|
| 4,761,373 A | * 8/1988 | Anderson et al. | 435/172.3 |
| 4,769,061 A | 9/1988 | Comai | 71/86 |
| 5,084,082 A | * 1/1992 | Sebastian | 71/90 |
| 5,331,107 A | 7/1994 | Anderson et al. | 800/235 |
| 5,369,022 A | * 11/1994 | Newhouse | 800/268 |

FOREIGN PATENT DOCUMENTS

| | | |
|---|---|---|
| EP | 0 360 750 | 3/1990 |
| EP | 0 375 875 | 7/1990 |
| WO | 90/14000 | 11/1990 |

OTHER PUBLICATIONS

Mazur et al (1989) Ann. Rev. Plant Physiol Plant Mol Biol 40: 441–470.*

Haughn et al., "A Mutation Causing Imidazolinone Resistance Maps to the Csr1 Locus of *Arabidopsis thaliana*," Plant Physiol., 92:1081–1085 (1990).

Haughn et al., "Sulfonylurea–resistant mutants of *Arabidopsis thaliana*," Mol. Gen. Genet., 204:430–434 (1986).

Chaleff et al., "Acetolactate Synthase Is the Site of Action of Two Sulfonylurea Herbicides in Higher Plants," Science, 224:1443–1445 (Jun. 29, 1984).

Kueh et al., Planta 153:166–171 (1981).

Matthews et al., Plant Physiol. 94:1180–1186 (1990).

Pinthus et al., Science 177:715–716 (1972).

Sebastian et al., Crop Science 27:948–952 (1987).

Siddiqui, Mutations in Wheat—Future Possibilities, Bio-–Technology in Agriculture and Forestry, vol. 13, Wheat, Ch. IV, pp. 549–578, Springer–Verlag, Berlin, ed. Bajaj, 1990.

Sebastian et al., Crop Science 29: 1403–1408 (1989).

Khamankar, J. Maharashtra Agric. Univ., 14(3):322–325 (1989).

* cited by examiner

*Primary Examiner*—Elizabeth F. McElwain
(74) *Attorney, Agent, or Firm*—Elaine Sale

(57) ABSTRACT

This invention is directed to a screening method for the selection of mutations which confer acetohydroxyacid synthase (AHAS) inhibiting herbicide resistance to wheat. After mutagenesis of wheat seeds, the seeds are soaked in an AHAS inhibiting herbicide-containing solution containing a particular class of AHAS inhibiting herbicide. After planting, the soil containing the seeds is sprayed with an AHAS inhibiting herbicide of the same class as that used in the seed soak step prior to the emergence of the seedlings from the soil. Those wheat seedlings which emerge and are normal in appearance demonstrate resistance to the class of AHAS inhibiting herbicides used in the seed soak and spraying steps. This invention is also directed to the wheat selections and seeds identified by the screening method.

11 Claims, 29 Drawing Sheets

CLASSIC POSTEMERGENCE—PLANT GROWTH OVER 4 WKS.

OUST POSTEMERGENCE—PLANT GROWTH OVER 4 WKS.

HEIGHT OF THREE M4 WHEAT MUTANTS AND FIDEL WILD TYPE, 6 WEEKS AFTER POSTEMERGENT TREATMENT WITH THREE IMIDAZOLINONE CHEMISTRIES.

AHAS INHIBITING HERBICIDE RESISTANT WHEAT AND METHOD FOR SELECTION THEREOF

This application is a continuation of Ser. No. 07/681,831 filed Apr. 8, 1991, now abandoned.

FIELD OF THE INVENTION

This invention relates to the use of a screening method for the selection of mutations which confer acetohydroxy acid synthase inhibiting herbicide resistance to wheat. This invention also relates to the resistant wheat developed by this method.

BACKGROUND OF THE INVENTION

The first enzymatic step common to the biosynthesis in plants of the branched chain amino acids (valine, leucine and isoleucine) is catalyzed by the enzyme acetohydroxyacid synthase (AHAS; also known as acetolactate synthase; E.C.4.1.3.18). AHAS catalyzes two parallel reactions: condensation of two moles of pyruvate to give rise to acetolactate, and condensation of a mole of pyruvate and a mole of alpha ketobutyrate to yield acetohydroxybutyrate. This enzyme is inhibited by the end products of the pathway (valine, leucine and isoleucine) and this is one of the known mechanisms of regulation of this pathway in higher plants.

AHAS is the target site of several classes of structurally unrelated herbicides. These herbicides include the imidazolinones, the sulfamoylureas, the sulfonylcarboxamides, the sulfonamides and the sulfonylureas.

Large scale commercial agriculture relies heavily on row-crop production practices. The availability of herbicides which selectively eliminate problem weeds while leaving crop plants undamaged is a major enabling component of these practices. Herbicides which control the majority of problem weeds are available for most major crops. The afore-mentioned AHAS inhibiting herbicides are a key element in weed control. These same herbicides, however, may miss important weeds in certain niche crop production areas. Also, currently used herbicides may have ecological problems or cost constraints attached to their use.

SUMMARY OF THE INVENTION

There is a need to develop varieties of wheat which are resistant to AHAS inhibiting herbicides. The development of such resistant varieties would permit wheat growers to use the AHAS inhibiting herbicides, whose use results in reduced application rates, reduced ground water contamination and reduced animal toxicity when compared to other classes of herbicides.

Accordingly, it is an object of this invention to develop a screening method for the selection of mutations which confer AHAS inhibiting resistance to wheat.

It is a particular object of this invention to develop a screening method for the selection of mutations which confer AHAS inhibiting imidazolinone herbicide resistance to wheat.

It is an additional object of this invention to identify wheat selections identified by the novel screening method.

These objects are accomplished by mutagenizing wheat seeds with a chemical mutagen. In a first screening step, seeds are soaked in an AHAS inhibiting herbicide-containing solution. In a second screening step after planting, soil containing the seeds is sprayed with an AHAS inhibiting herbicide prior to the emergence of seedlings from the soil. Those wheat seedlings which emerge demonstrate resistance to AHAS inhibiting herbicides.

BRIEF DESCRIPTION OF THE DRAWINGS

Note: The chemical names of the trademarked herbicides and Compound Numbers in this Brief Description of the Drawings are set forth in the Detailed Description of the Invention portion of this application.

DETAILED DESCRIPTION OF THE INVENTION

Figure 1:
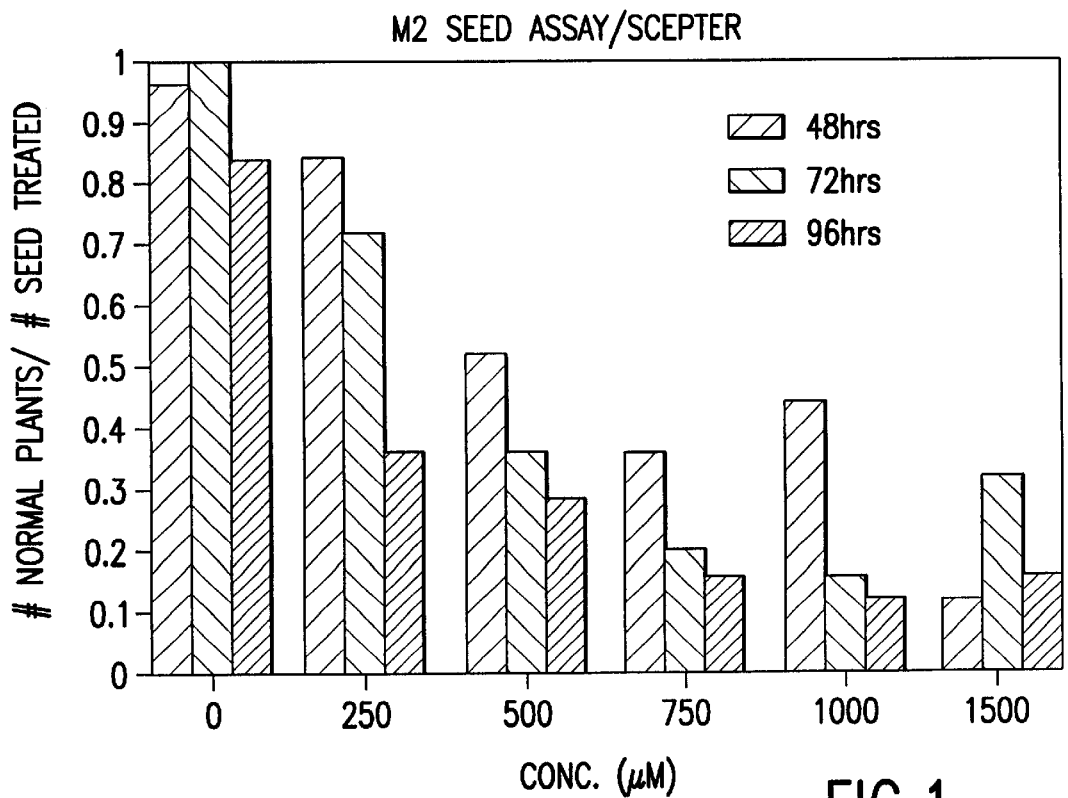
FIG. 1 depicts the effect of increasing the concentration of the imidazolinone herbicide SCEPTER™ upon the ratio of the number of plants which have a normal appearance versus the number of seeds soaked in an imidazolinone herbicide-containing solution.

This invention is directed to a novel method for screening for the selection of mutations which confer AHAS inhibiting herbicide resistance to wheat. Wheat seeds are mutagenized with a chemical mutagen by conventional means. In a first screening step, mutagenized seeds are soaked in an AHAS inhibiting herbicide-containing solution containing a particular class of AHAS inhibiting herbicide by adapting a published procedure for soybeans to wheat.

In a novel second screening step, the seeds are then planted in soil and subjected to spraying with an AHAS inhibiting herbicide of the same class as that used in the seed soak step prior to emergence of seedlings from the soil. Those wheat plants which emerge and have a normal appearance are considered to be resistant to the class of AHAS inhibiting herbicides used in the two step screen. These plants therefore have the benefit of being able to be planted and their area treated with a class of AHAS inhibiting herbicides so as to eliminate problem weeds while the wheat plants remain undamaged. The inheritance of the AHAS inhibiting herbicide resistance trait is demonstrated by testing several generations of seeds from the initial mutants for resistance to applications of a class of AHAS inhibiting herbicides. The resulting plants may be, but are not necessarily, cross-tolerant to classes of AHAS inhibiting herbicides other than that used in the two step screen.

The mutagenesis of the seeds is achieved by conventional means using a chemical mutagen. One procedure is that of Kueh and Bright (Kueh, J. S. H. and Bright, S. W. J., *Planta*, 153, 166–171 (1981), wherein seeds are soaked in water, air is bubbled through the seeds, followed by treatment with a chemical mutagen such as sodium azide. The seeds are then rinsed with water and dried. The use of sodium azide in this procedure is particularly preferred.

Other chemical mutagens and procedures for their use include N-methyl-N-nitrosourea and N-ethyl-N-nitrosourea (Fluhr, R. and Cseplo, A., *Methods Enzymol.* (*Plant Mol. Biol.*), 118, 611–623 (1986)), ethyl methanesulfonate (Sebastian, S. A., et al., *Crop Sci.*, 29, 1403–1408 (1989)), and hydroxylamine and hydrazine (Khamankar, Y. G., *J. Maharashtra Agric. Univ.*, 14, 322–325 (1989)).

The mutagenized seeds are then screened for resistance to AHAS inhibiting herbicides. Initially, in vitro screens evaluating herbicide tolerance of isolated wheat embryos, half seeds and whole seeds, are investigated. However, these screens are time consuming and problematic due to contamination problems and variable response of the wheat. Therefore, another type of screen is used. This procedure is derived from a protocol developed by Sebastian and Chaleff (Sebastian, S. A. and Chaleff, R. S., *Crop Science*, 27, 948–952 (1987)) for selection of herbicide tolerant soybean. This screening procedure involves soaking whole, mature wheat seeds in an AHAS inhibiting herbicide-containing solution containing a particular class of AHAS inhibiting herbicide for a set period of time after which the seeds are planted in a sterile soil mixture.

Various classes of AHAS inhibiting herbicides include the imidazolinones, the sulfamoylureas, the sulfonylcarboxamides, the sulfonamides and the sulfonylureas.

Examples of imidazolinone herbicides which are used in the seed soak screening step include 2-(4-isopropyl-4-methyl-5-oxo-2-imidiazolin-2-yl)-nicotinic acid, 2-(4-isopropyl)-4-methyl-5-oxo-2-imidazolin-2-yl)-3-quinolinecarboxylic acid, 5-ethyl-2-(4-isopropyl-4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, 5-formyl-2-(4-isopropyl-4-methyl-5-oxo-2-imidazolin-2-yl)-nicotinicacid, 5-(dimethyl acetal), 3-(4-isopropyl-4-methyl-5-oxo-2-imidazolin-2-yl)-2-methyl-crotonic acid), 2-(4-isopropyl-4-methyl-5-oxo-2-imidazolin-2-yl)-5-methylnicotinic acid, and a mixture of methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate. The use of 5-ethyl-2-(4-isopropyl-4-methyl-5-oxo-2-imidazolin-2-yl)-nicotinic acid and 2-(4-isopropyl-4-methyl-5-oxo-2-imidazolin-2-yl)-nicotinic acid is preferred. The use of 5-ethyl-2-(4-isopropyl-4-methyl-5-oxo-2-imidazolin-2-yl)-nicotinic acid is particularly preferred.

Examples of sulfamoylurea herbicides which are used in the seed soak screening step include 1-(4-methoxy-6-methyl-s-triazin-2-yl)-3-[(o-propionyl-phenyl)sulfamoyl]urea, 1-(4,6-dimethoxy-2-pyrimidinyl)-3-[(o-propionylphenyl)sulfamoyl]urea, 1-[(o-acetyl-phenyl) sulfamoyl]-3-( 4-methoxy-6-methyl-2-pyrimidinyl)-urea, and 1-[(o-acetylphenyl)sulfamoyl]-3-(4-methoxy-6-methyl-s-triazin-2-yl)urea. Examples of sulfonylcarboxamide herbicides include 2-acetamido-2,3-dimethyl-N-(p-tolylsulfonyl)butyramide and 2-acetamido-N-[(p-chlorophenyl)sulfonyl]-2,3-dimethylbutyramide. An example of a sulfonamide is N-[2,6-difluorophenyl]-5-methyl-(1,2,4)-triazolo-[1,5a]-pyrimidine-2-sulfonamide. Examples of sulfonylureas include 2-[4,6-bis=(difluoromethoxy)pyrimidin-2-ylcarbamoylsulfamoyl] benzoic acid, 1-(4,6-dimethoxypyrimidin-2-yl)-3-(dimethoxycarbamoyl-2-pyridylsulfonyl)urea, the methyl ester of o-[[3-(4,6-dimethylpyrimidin-2-yl)ureido]sulfonyl]-benzoic acid) and the ethyl ester of o-[[(4-chloro-6-methoxy-2-pyrimidinyl)carbamoyl]sulfamoyl]benzoic acid).

If the seed soak were the only screen to be used, it would be conducted as follows: After drying, the seeds are planted and the number of germinating seeds is counted after a predetermined period of time, such as three or four weeks after planting. The size and appearance of the seedlings is also noted. Seeds which germinate and produce seedlings of normal size and appearance may be resistant to AHAS inhibiting imidazolinone herbicides.

However, the seed soak screen may result in the possibility of "escapes" or false positives surviving the herbicide treatment. To eliminate false positives, a pre-emergent herbicide treatment is used as a second screen.

After the seed soak step, the wheat seeds are planted in soil. If desired, the soil may be watered. The soil containing the seeds is then sprayed, prior to the emergence of seedlings from the soil, with an AHAS inhibiting herbicide in a solution containing water or other acceptable aqueous or organic solvents. The concentration of herbicide to be sprayed is ascertained for each imidazolinone by small scale trials.

The AHAS inhibiting herbicide used in the seed spraying step is selected from the same class as that used in the seed soak step. The particular herbicide chosen may be the same or different in the two screening steps, but in each case, the herbicides must be chosen from the same class of AHAS inhibiting herbicides. The classes of herbicides and examples of each class used in the seed spraying step are as described previously with regard to the seed soak step.

The seeds subjected to the two step screen are then evaluated after emergence of seedlings from the soil. Growth which is normal in size, yield and appearance indicates that the wheat contains a mutation which results in the desired resistance to AHAS inhibiting herbicides.

Wheat with high levels of tolerance for AHAS inhibiting herbicides is selected via this two step screening protocol. This screening system allows the preferential selection of strongly resistant wheat plants by exposing the seed to herbicide rates lethal to wild-type wheat plants at two points in the screen, the seed soak treatment and the preemergent application. This double exposure to herbicide eliminates false positives and may serve to eliminate weakly resistant mutants. The resistant wheat plants are resistant to herbicides of the class used in the two step screen. The plants may be in some instances cross-tolerant to one or more other classes of AHAS inhibiting herbicides, but such cross-tolerance need not be present.

The examples presented below are illustrative of this invention with the imidazolinone class of AHAS inhibiting herbicides. The other classes of AHAS inhibiting herbicides are also within the scope of this invention because their mechanism of action is the same as that of the imidazolinones. All AHAS inhibiting herbicides act by the same mechanism of action; they target the AHAS enzyme, thereby blocking the biosynthesis of valine, leucine and isoleucine. By blocking this activity of AHAS, the herbicides inhibit plant metabolism, leading to the death of the plant.

When the two step screening method of this invention is used with the imidazolinone class of herbicides, wheat selections are obtained which are resistant to the imidazolinone class of herbicides. The herbicide-resistant wheat has an increased tolerance to imidazolinones of up to 50-fold as compared to the non-mutagenized, unselected wheat. The imdazolinones have been shown to inhibit the enzyme AHAS, one of the first enzymes in branched chain amino acid biosynthesis. The wheat selections are assayed by in vitro enzyme assays (described in the examples below) and are shown to have AHAS activity which is insensitive to inhibition by imidazolinones. However, there is little or no evidence of cross tolerance to other chemistries with a similar mode of action upon AHAS either by whole plant or enzyme studies.

Out of 117,000 wheat seeds screened, four wheat plants are selected for their resistance properties. These four mutant selections are designated FS1, FS2, FS3 and FS4. Samples of seeds of these wheat plants have been deposited on Mar. 28, 1991 with the American Type Culture Collection, 10801 University Boulevard, Manassas, Va. 20110-2209. and have been assigned accession numbers as follows:

| Wheat Mutant | Accession Number |
| --- | --- |
| FS1 | ATCC 40994 |
| FS2 | ATCC 40995 |
| FS3 | ATCC 40996 |
| FS4 | ATCC 40997 |

Based on genetic data, the selected wheat mutants, FS1, FS2, FS3, and FS4, are allelic and appear to be the result of a single mutational event. The tolerance is inherited as a single genetic locus and is dominant or semidominant in expression. The increase in herbicide tolerance is shown to have no deleterious effects on grain yield either in the presence or absence of the imidazolinone herbicides tested.

The inheritance of the mutations in the resistant wheat selections is confirmed by testing several generations of progeny of the seeds, as well as intercrosses of the mutant selections. The test seeds are subjected to both pre-emergence and post-emergence applications of various classes of AHAS inhibiting herbicides. The size, yield and appearance of the seedlings are observed and compared to untreated controls (Fidel) and to controls (Fidel) subjected to the same two step screening procedure.

Results of these tests, as described in the examples, indicate that the mutations conferring resistance to imidazolinones are inherited from generation to generation of plants derived from the FS1, FS2, FS3 and FS4 selections. The specificity of the resistance is demonstrated by the data which indicate that the mutant selections are not resistant to other classes of AHAS inhibiting herbicides such as sulfonylureas, sulfamoylureas, sulfonamides or sulfonylcarboxamides.

In a second embodiment of this invention, two different classes of AHAS inhibiting herbicides are used in the two step screening method. In the seed soak step, a herbicide from one class is used. In the spraying step, a herbicide from a second class is used. The resulting plant selections which survive and grow normally are resistant to both classes of herbicides. Although the frequency of mutations conferring resistance which are selected for is greatly reduced, because of the different classes of herbicides used, if the number of seeds screened is large enough, double resistant selections are obtained.

In order that this invention may be better understood, the following examples are set forth. The examples are for the purpose of illustration only and are not to be construed as limiting the scope of the invention.

EXAMPLE 1

Development of a Two Step Seed Screen

1. Seed Mutagenesis

Five thousand seeds of "Fidel", a French winter wheat, are mutagenized following the procedure of Kueh and Bright (Kueh, J. S. H. and Bright, S. W. J., *Planta*, 153, 166–171 (1981). The wheat seeds are soaked in water for 18 hours at 5° C. and then air is bubbled through the seeds for six hours at 20° C. This is followed immediately by treatment with 1 mM sodium azide, a chemical mutagen, at pH3 for two hours. The seeds are rinsed with water for 30 minutes and then spread in a shallow layer onto paper towels to dry. Once dry, the seeds are planted in the field.

The wheat plants are grown to maturity and the $M_2$ seed is harvested. Approximately 117,000 wheat seeds are harvested and used to screen for imidazolinone-resistant wheat. The germination frequency of this material is 100%.

2. Step 1: Seed Soak

Following the protocol developed by Sebastian and Chaleff, wheat seeds are surface disinfested in 70% EtOH for 30 seconds followed by disinfestation in 50% solution containing 2.625% sodium hypochlorite, with 1–2 drops of Tween 20™ (a non-ionic polyethylene sorbitan monolaurate surfactant, available under the registered trademark of Atlas Chemical Industries) per 100 ml of solution, for 30 minutes under vacuum with gentle agitation provided by a stir plate. The seeds are rinsed in sterile distilled water and then soaked in a herbicide concentration for a set period of time, as described below. Sets of twenty-five seeds are placed into 25 ml of the herbicide solution described below in a sterile 100×15 mm plastic petri dish and soaked for the designated time. The seeds are rinsed with water, dried with paper towels and planted (25 seeds/flat) approximately ½" deep in 6×8 inch peat flats containing a moist, sterile, artificial soil, Metro Mix 350™ (Grace Company, Cambridge, Mass.). The treatments are evaluated at four weeks after treatment. The herbicides, rates and time periods evaluated are described below:

| Experiment 1: | |
|---|---|
| ARSENAL ™: | 0, 1, 10, 50, 100, 500 µM |
| SCEPTER ™: | 0, 1, 10, 50, 100, 500 µM | for 48 hours. Each treatment is replicated four times. (ARSENAL™ and SCEPTER™ are registered trademarks of American Cyanamid Company. ARSENAL™ is 2-(4-isopropyl-4-methyl-5-oxo-2-imidazolin-2-yl)-nicotinic acid and is described in U.S. Pat. No. 4,798,619; SCEPTER™ is 2-(4-isopropyl-4-methyl-5-oxo-2-imidazolin-2-yl)-3-quinolinecarboxylic acid and is described in U.S. Pat. No. 4,798,619.)

ARSENAL inhibits seed germination and seedling growth with increasing concentration. While some potential false positives are observed visually at concentrations up to 50 uM, higher concentrations totally inhibit seedling growth. At these concentrations, 100 and 500 uM, some susceptible seeds germinate, but the shoots are small, twisted and generally abnormal in appearance.

While SCEPTER™ also inhibits seedling growth with increasing concentration, by three to four weeks, the seedlings recover, as observed visually. In fact, seedlings treated with 1–100 uM are indistinguishable from controls and seedlings treated with 500 uM are slightly shorter than controls.

| Experiment 2: | |
|---|---|
| ARSENAL ™ | 0, 10, 50, 100, 500 µM |
| SCEPTER ™ | 0, 100, 250, 500, 750, 1000 µM | for 48 hours. Each treatment is replicated two times.

ARSENAL™ is retested at the same concentrations as the previous experiment and the same results are obtained as described above. In this study, the SCEPTER™ concentration is increased to a maximum of 1000 uM. By the end of the study, it is evident from visual observation that this concentration is still not high enough to prevent "escapes". The duration of exposure to the herbicide also appears to have an effect on the number of false positives. In experiment 1, the seeds soak for a few hours longer and some root elongation occurs; however, the seeds in this experiment do not all exhibit radicle emergence when the herbicide treatment is terminated. The effect of the duration of the seed soak upon the herbicide concentration necessary to prevent "escapes" is investigated in the following experiment.

| Experiment 3: | |
|---|---|
| ARSENAL ™ | 0, 50, 75, 100 µM |
| SCEPTER ™ | 0, 250, 500, 750, 1000, 1500 µM |
| PURSUIT ™ | 0, 250, 500, 750, 1000, 1500 µM |
| Compound 1: | 0, 500, 1000, 1500, 2000 µM | for 48, 72 or 96 hours. Each treatment is replicated two times. (PURSUIT™ is a registered trademark of American Cyanamid Company. PURSUIT™ is 5-ethyl-2-(4-isopropyl-4-methyl-5-oxo-2-imidazolin-2-yl)-nicotinic acid and is described in U.S. Pat. No. 4,798,619. Compound 1 is 2-acetamido-N-[(p-chlorophenyl)sulfonyl]-2,3-dimethyl-butyramide, and is described in U.S. Pat. No. 4,992,094.)

Figure 2:
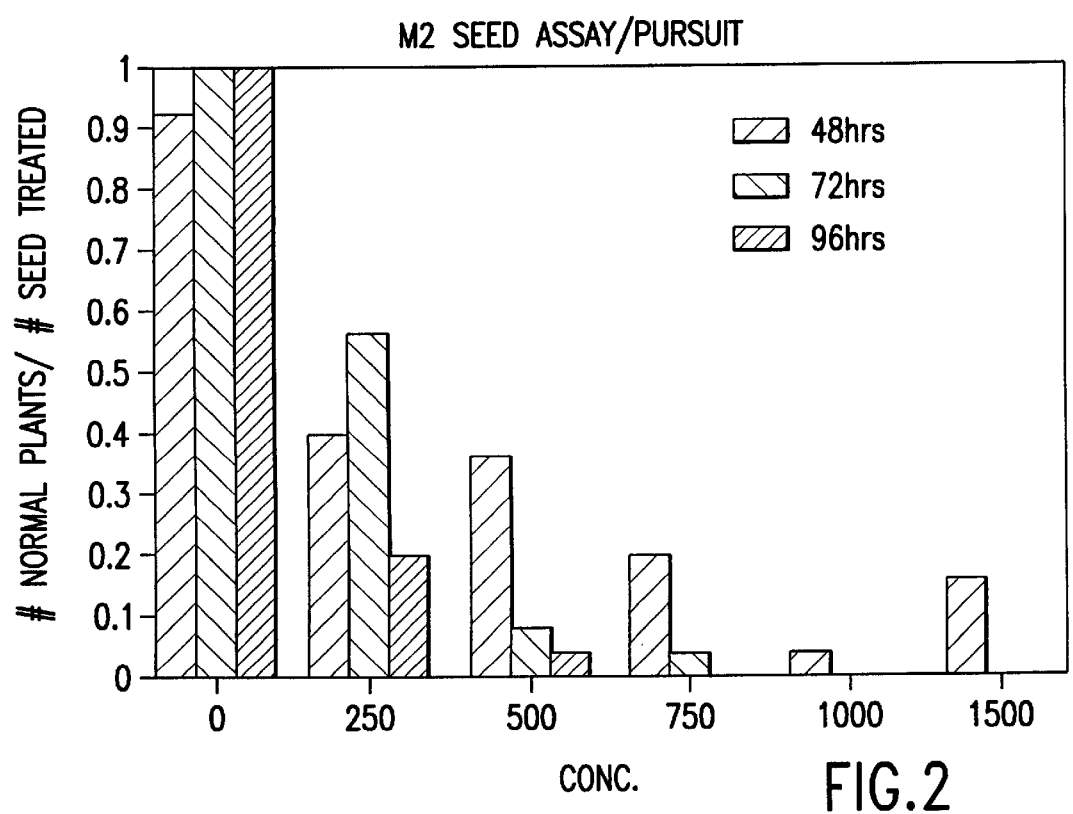
FIG. 2 depicts the effect of increasing the concentration of the imidazolinone herbicide PURSUIT™ upon the ratio of the number of plants which have a normal appearance versus the number of seeds soaked in an imidazolinone herbicide-containing solution.
Figure 3:
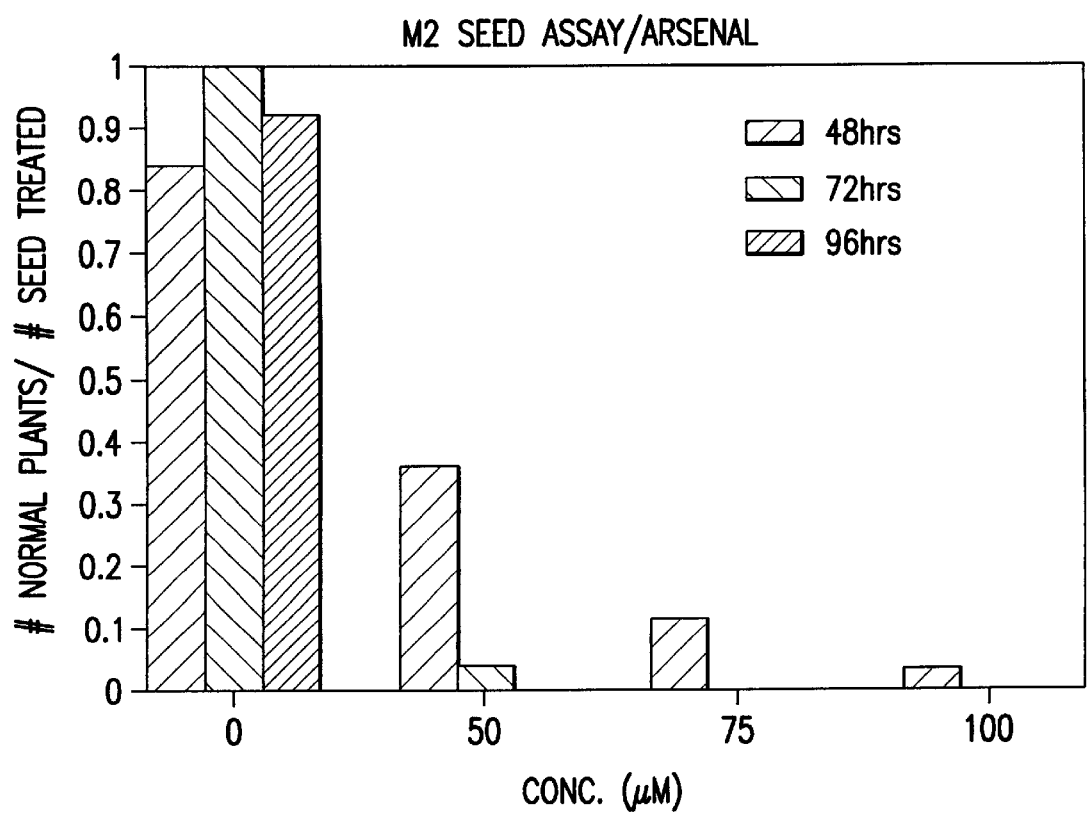
FIG. 3 depicts the effect of increasing the concentration of the imidazolinone herbicide ARSENAL™ upon the ratio of the number of plants which have a normal appearance versus the number of seeds soaked in an imidazolinone herbicide-containing solution.

In this study, the imidazolinone herbicides ARSENAL™, SCEPTER™, PURSUIT™, and the sulfonylcarboxamide Compound 1 are evaluated as selective agents in the seed soak screen. The interaction of seed soak duration with herbicide concentration is also evaluated. FIGS. 1–3 present the results of imidazolinone herbicide treatments. When the seeds are soaked for 48 hours, the number of "normal" plants decreases with increasing herbicide concentration. However, there are normal plants even at the highest herbicide concentrations tested. As the length of exposure to herbicide increases, the herbicide concentration necessary for lethality is reduced. ARSENAL™ at 50 uM is sufficient if the exposure is greater than 72 hours, however 75 uM is necessary if the length of exposure is less. SCEPTER™ is not effective at any of the herbicide/exposure length combinations. In contrast, treatment of the seeds with either 1000 uM PURSUIT™ for 72 hours or 750 uM PURSUIT™ for 96 hours prevents the survival of potential false positives. Compound 1 does not have an inhibitory effect on either seed germination or seedling growth.

| Experiment 4: | |
|---|---|
| SCEPTER ™: | 0, 500, 1000, 1500, 2000 µM | for 3, 4, 7 and 10 days. Each treatment is replicated two times.

The protocol is as described above except that 35 seeds are soaked per petri dish; 25 seeds are still planted per flat. This experiment is repeated twice. (Note: The 7 and 10 day plantings become contaminated with fungus in the first experiment and are discarded. In the second experiment, the fungicide, Captan, is added to the soaking solution to prevent contamination.)

Soaking durations of seven and ten days are too long a period for use with wheat seeds. By this time, shoot elongation starts to occur in SCEPTER™ at concentrations up to 1000 uM; fungal contamination also starts to be a problem with these time periods.

Visual results are similar to those observed for PURSUIT™ in Experiment 3. Either 1000 or 1500 uM SCEPTER™ for three days are suitable for selection of imidazolinone resistant mutants with the problem of false positives minimized.

3. Step 2: Pre-emergence Herbicide Application

A series of experiments is performed to determine the appropriate herbicide rate for this pre-emergent spray treatment. Wheat seed of the susceptible cultivar Fidel is planted in Metro Mix 350™ in 6×8 inch peat flats at a rate of 100 seeds per flat. The flats are watered prior to herbicide treatment. Three flats are sprayed per treatment. The herbicides are applied with a laboratory belt sprayer at a rate of 950 liters per hectare (L/ha) at a belt speed of 12.8 sec/rev using sprayer nozzle #40015E (Teejet™ Spraying Systems). After three to four weeks, the treatments are evaluated by visual observation for toxicity to the wheat seeds/seedlings. PURSUIT™ and SCEPTER™ are most effective at 300–350 g/ha, while ARSENAL™ is most effective when sprayed at 40–50 g/ha preemergence.

4. Screening and Selection of Herbicide Resistant Mutants

PURSUIT™ is used as an exemplary imidazolinone for screening for herbicide resistance. $M_2$ wheat seeds are surface disinfested in 70% EtOH for 30 seconds followed by disinfestation in 50% solution containing 2.625% sodium hypochlorite as described above. The seeds are then rinsed three times with sterile distilled $H_2O$ and placed into sterile plastic 100×15 mm petri dishes, 250 seeds per dish. Twenty-five ml of 1000 mM PURSUIT™ solution is added to each dish and the seeds are soaked in this solution in the dark for 3 days. The seeds are then drained, blotted dry on paper towels and planted in sterile 6×8 inch peat flats containing Metro Mix with 1000 seeds planted/flat. The flats are watered and sprayed immediately with 300 grams per hectare (g/ha) PURSUIT™. The herbicide is applied with a laboratory belt sprayer at a rate of 950 L/ha with a belt speed of 12.8 sec/rev using sprayer nozzle #40015E. After four weeks, the seedlings are evaluated for herbicide tolerance. The $M_2$ wheat seed is screened in lots of 25,000 seeds at a time. Out of approximately 117,000 $M_2$ wheat seeds put through the two-step screen for herbicide resistance, four wheat plants are selected which are resistant to PURSUIT™.

Figure 4:
FIG. 4 and 5 depict the appearance of imidazolinone herbicide-resistant wheat, treated with a seed soak plus pre-emergent spray containing PURSUIT™, compared with untreated, non-resistant wheat. The resistant wheat is in the left-most flat in FIG. 4; the resistant wheat is in the middle flat in FIG. 5.
Figure 5:
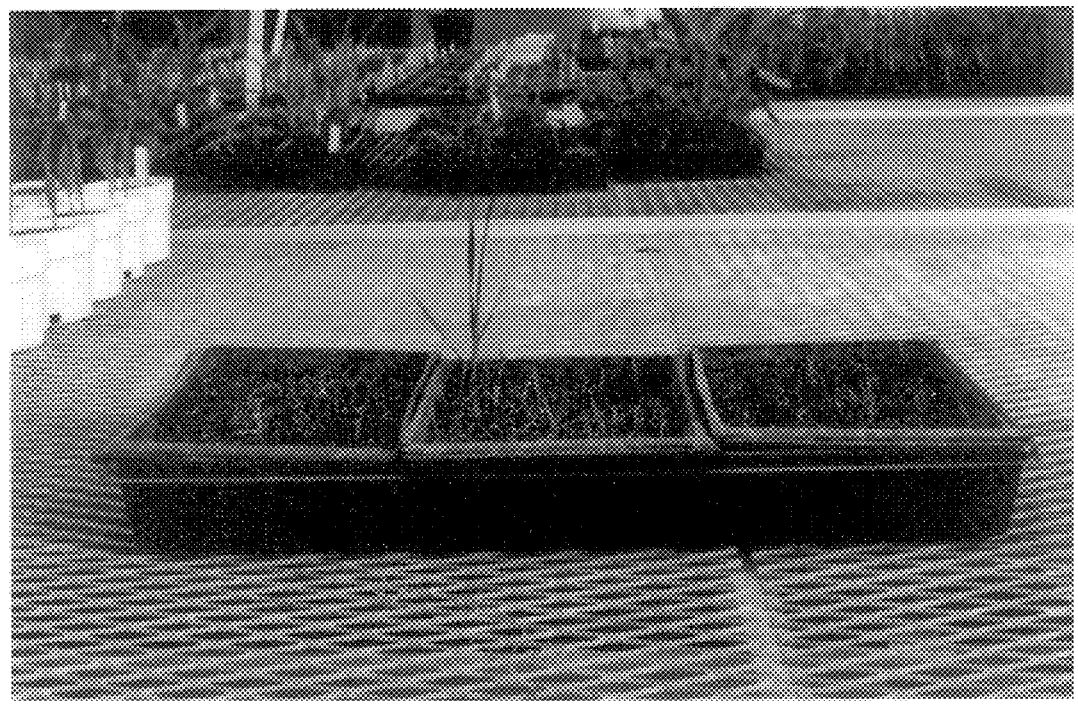

These plants are quite striking in their appearance as compared to non-resistant wheat. Two of these mutant selections are depicted in FIGS. 4 and 5. The resistant wheat is in the left-most flat in FIG. 4; the resistant wheat is in the middle flat of FIG. 5. These four mutant selections are designated FS1, FS2, FS3, and FS4. The resistant plants are transplanted into 7.5 inch peat pots in Metro Mix 350™.

EXAMPLES 2–5

Characterization of Herbicide Resistant Mutants

EXAMPLE 2

Inheritance of Herbicide Resistance Trait

1. $M_3$ Plant Screen: In vivo $M_3$ plants from the four initial plant selections (labelled FS1, FS2, FS3 and FS4) are screened for PURSUIT™ resistance. Five $M_3$ seeds from each mature infloresence of these initial $M_2$ mutants are disinfested in 70% EtOH for 30 seconds followed by disinfestation in 50% solution containing 2.625% sodium hypochlorite (as described above) for 20 minutes under vacuum with gentle agitation provided by a stir plate. The seeds are rinsed two times in sterile distilled water.

Each set of five seeds is then placed into 10 ml of a 1500 uM solution of PURSUIT™ in a sterile 60×15 mm plastic petri dish and soaked for three days. The seeds are rinsed with water, dried with paper towels and planted approximately ½" deep in 6×8 inch peat flats containing moist, sterile Metro Mix 350™. These flats are sprayed preemergence with 300 g/ha of PURSUIT™. Controls include $M_3$ seeds from each resistant selection which are disinfested as previously described, soaked in sterile distilled water for three days and then planted. In addition, unselected susceptible Fidel wheat is disinfested as described above and one-half of the seeds treated with PURSUIT™ (seed soak and spray procedure) and the other half are soaked in water alone. The herbicide is applied with a laboratory belt sprayer at a rate of 950 L/ha with a belt speed of 12.5 sec/rev using sprayer nozzle #40015E.

Four weeks after receiving the initial seed soak, the $M_3$ wheat plants are rated according to whether the plants are herbicide resistant, herbicide damaged or dead. The herbicide resistant plants are transplanted individually to 7.5 inch Azalea pots with Metro Mix $_{350}$™. A fertilizer, Osmocote™ (Sierra Company, Milpita, Calif.) is added as a top dressing one week after the plants are transplanted. In addition the plants are fertilized regularly with Peter's 20-20-20™ (Grace Company, Cambridge, Mass.). Individual plants are rated against Fidel untreated controls.

Figure 6:
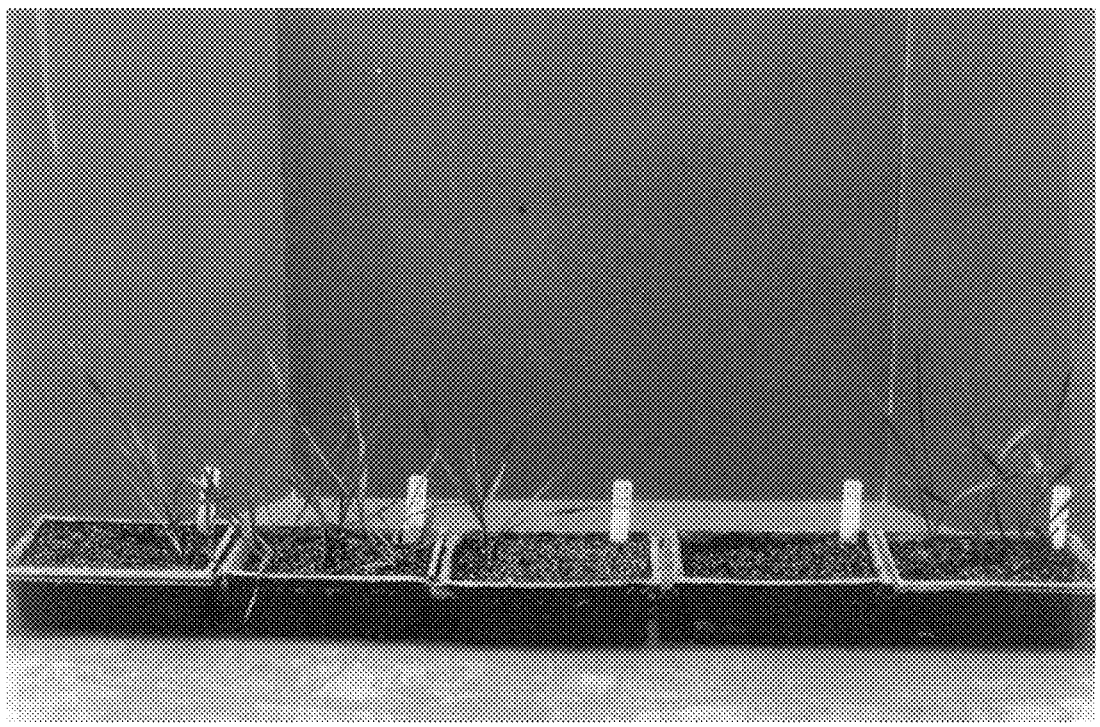
FIG. 6 depicts the appearance of wheat grown from $M_3$ seedlings, which are progeny of FS4.
Figure 7:
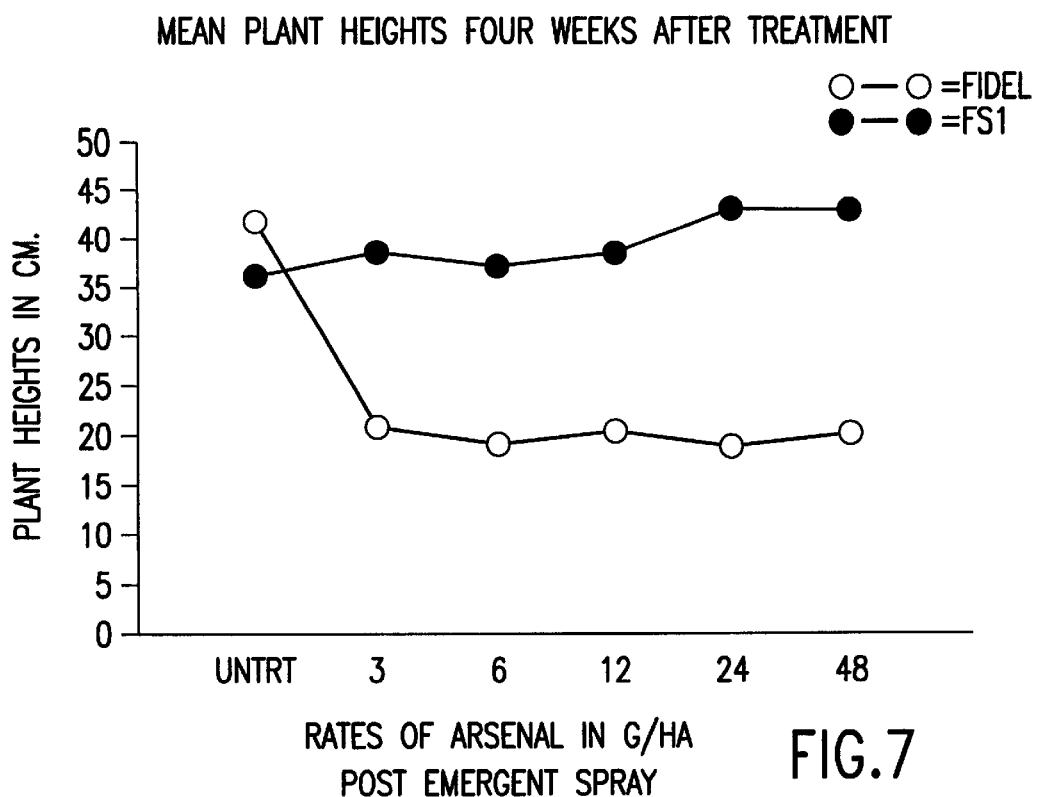
FIG. 7 depicts a comparison of plant height (in cm.) of wild-type wheat (Fidel) versus bulked $M_3$–$M_4$ seed from FS1 four weeks after post-emergence treatment with ARSENAL™.
Figure 8:
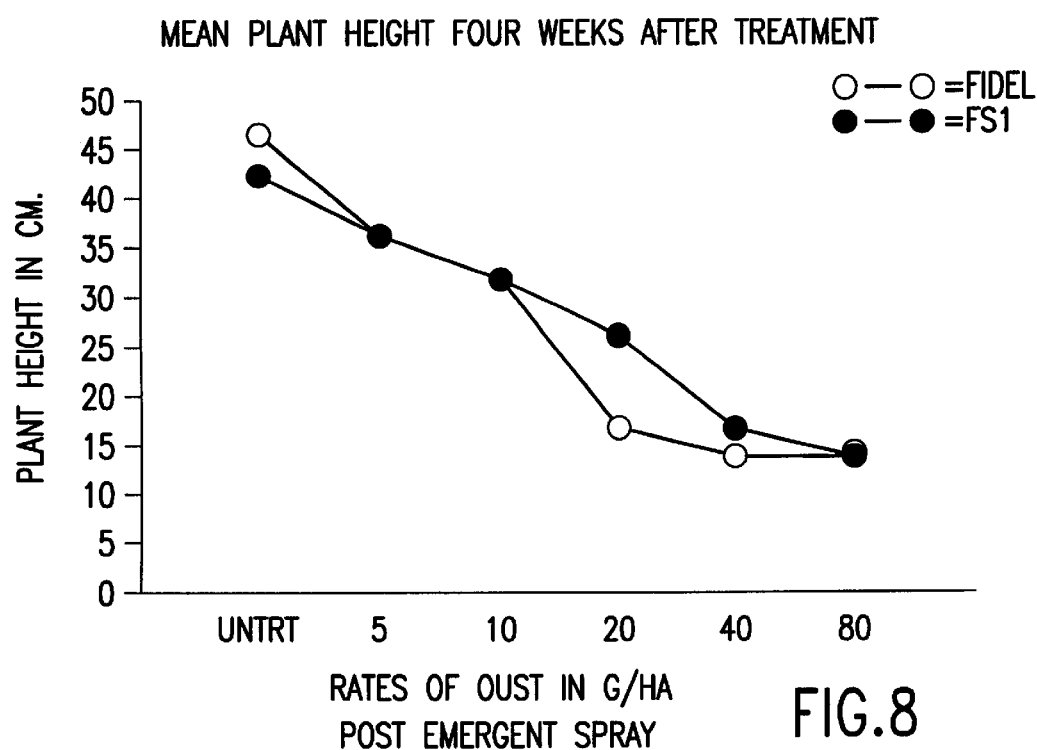
FIG. 8 depicts a comparison of plant height (in cm.) of wild-type wheat (Fidel) versus bulked $M_3$–$M_4$ seed from FS1 four weeks after post-emergence treatment with OUST™.
Figure 9:
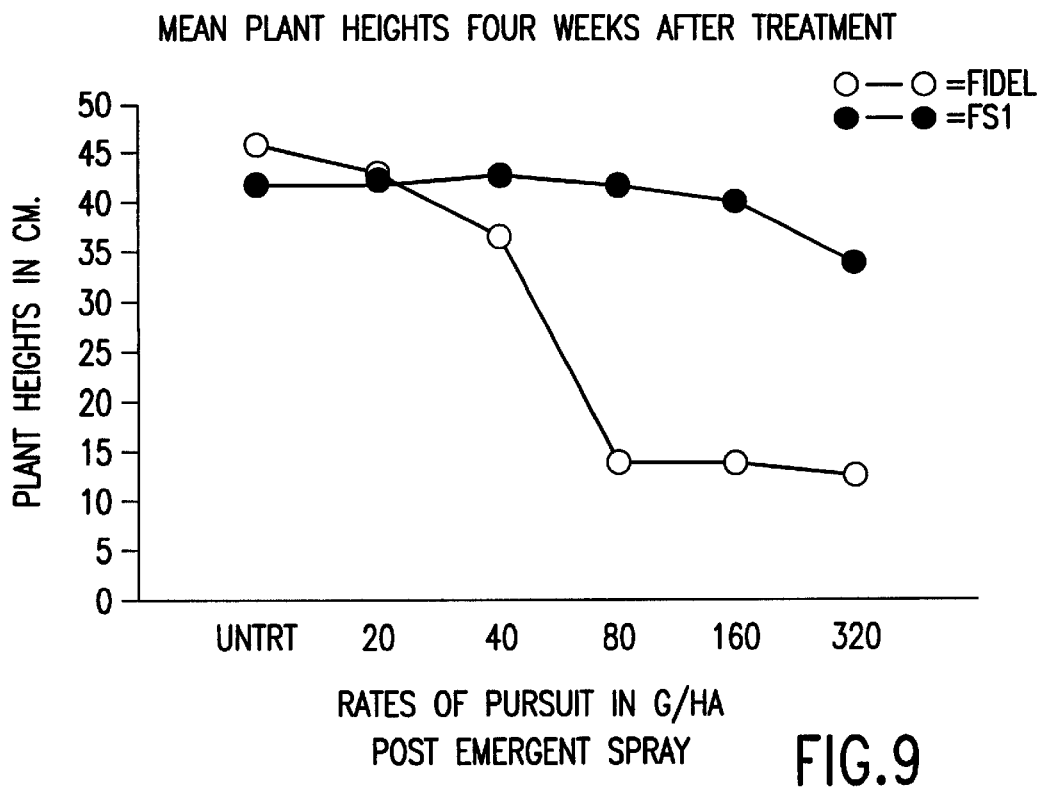
FIG. 9 depicts a comparison of plant height (in cm.) of wild-type wheat (Fidel) versus bulked $M_3$–$M_4$ seed from FS1 four weeks after post-emergence treatment with PURSUIT™.
Figure 10:
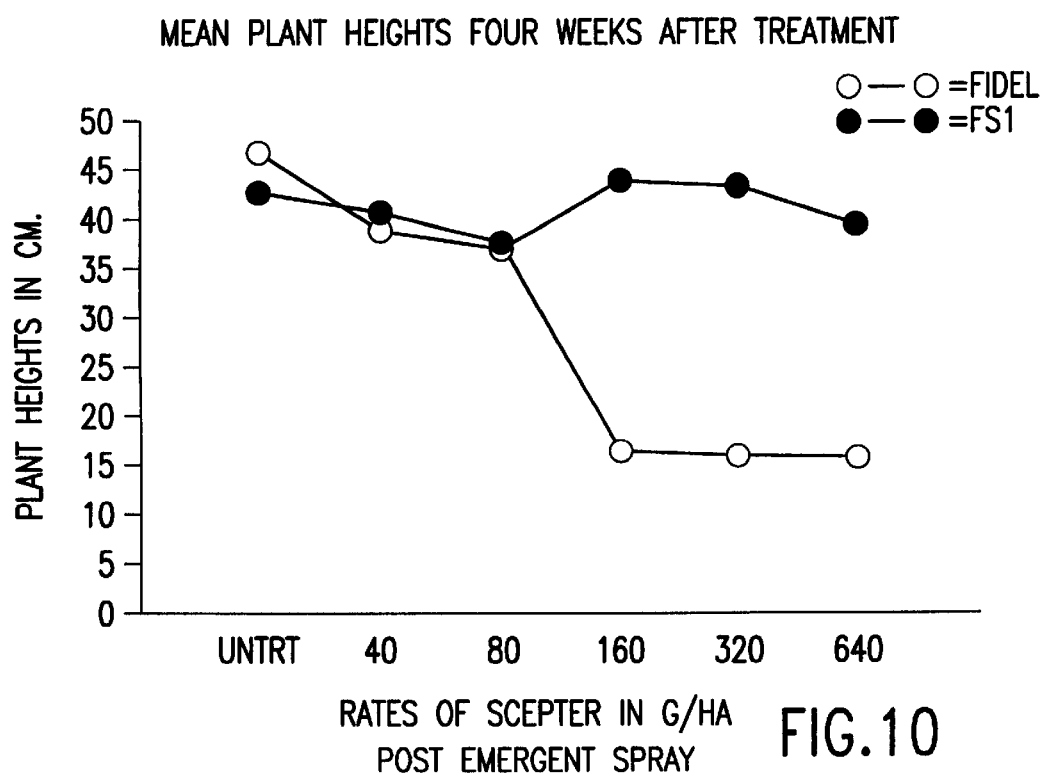
FIG. 10 depicts a comparison of plant height (in cm.) of wild-type wheat (Fidel) versus bulked $M_3$–$M_4$ seed from FS1 four weeks after post-emergence treatment with SCEPTER™.
Figure 10A:
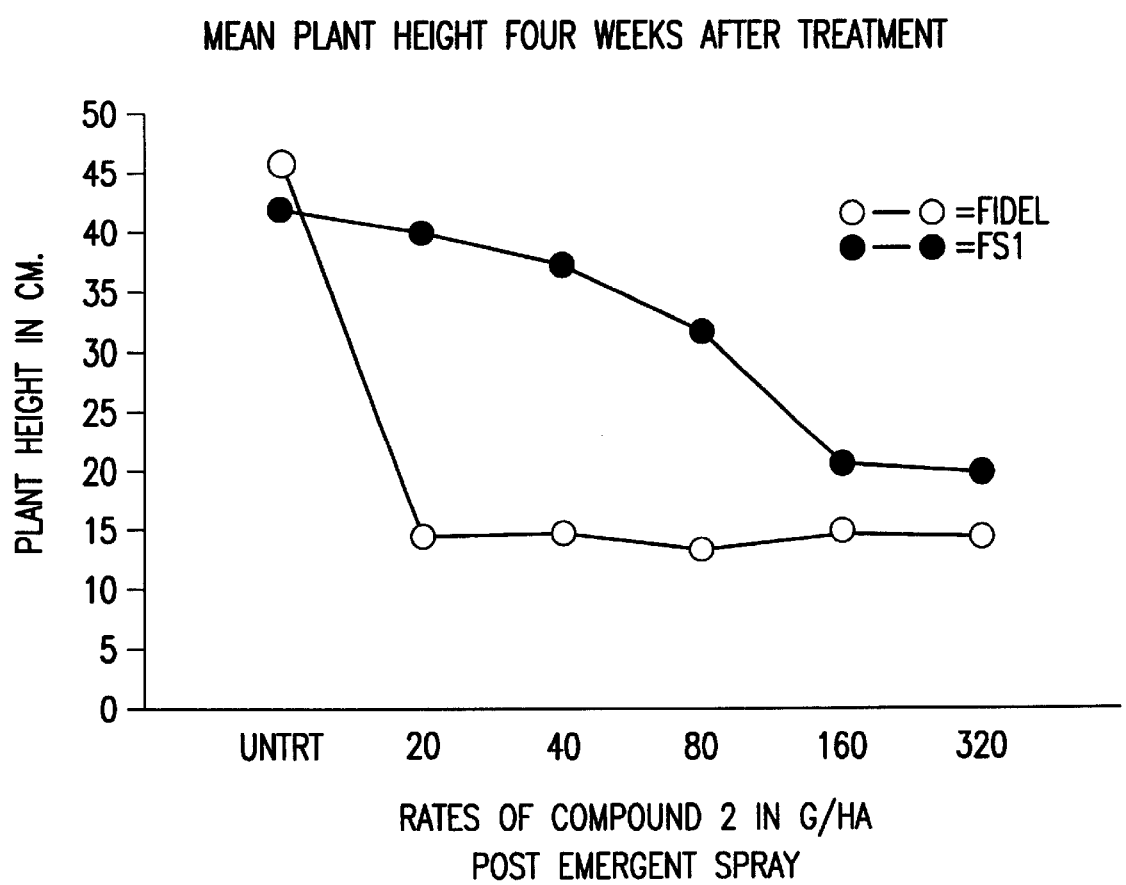
FIG. 10a depicts a comparison of plant height (in cm.) of wild-type wheat (Fidel) versus bulked $M_3$–$M_4$ seed from FS1 four weeks after post-emergence treatment with Compound 2.

Non-mutagenized, non-selected Fidel seed does not survive when treated with PURSUIT™ at 1500 uM (seed soak) and 300 g/ha (preemergent application). This same material, when soaked in sterile distilled water and not sprayed, germinates within 1–2 weeks with an average germination frequency of 63.3% (average of two sets of controls). $M_3$ material, when soaked in sterile distilled water and not sprayed, has a germination frequency of 53.3%. Seed of the resistant wheat selections, treated with PURSUIT™, germinates with the following frequencies: FS1-60%, FS2-47.5%, FS3-41.2% and FS4-55%. Many of the $M_3$ seedlings exposed to herbicide treatment grow at the same rate as untreated controls; however, some seedlings which are progeny of FS4 are affected by the herbicide, exhibiting symptoms of stunting, twisting and/or chlorotic striping (FIG. 6). Most of these are capable of survival and further growth. Plant height three weeks after herbicide treatment is presented in Table 1.

Table 1: $M_3$ Plant Screen: Results of screening $M_3$ progeny of the four initial wheat selections in the Seed Soak/ Preemergence Application screen.

| Selection | No. Heads Tested | No. of Plants[1] | Ave. Shoot Height (cm) | Range Shoot Heights (cm) |
|---|---|---|---|---|
| FS1 | 16 | 48/80 | 9.1 | 2–15 |
| FS2 | 16 | 38/80 | 11.7 | 5–18 |
| FS3 | 17 | 35/85 | 8.0 | 1–14.5 |
| FS4 | 17 | 44/85 | 21.1 | 5–28 |
| Control 1 | —[2] | 6/15 | 19.0 | 10–26 |
| Control 2 | —[2] | 13/15 | 21.2 | 8–30 |
| Control $M_3$ | 3 | 8/15 | 28.9 | 27–31 |

[1]Number of plants raised/number of seeds planted.
[2]Seeds rather than heads are tested in Controls 1 and 2.
Control 1 = Susceptible wheat seed (Fidel) soaked in sterile distilled water.
Control 2 = Susceptible wheat seed (Fidel) soaked in herbicide solution.
Control $M_3$ = $M_3$ seed from the initial selections soaked in sterile water.

Plant heights range from 1 to 28 cm for the mutant selections. This demonstrates the variability in the degree of herbicide tolerance. Control plants range from 8 to 31 cm in height. All of the plants are transplanted into Metro Mix 350™ in 7 ½ inch peat pots and used to make the crosses described in part 4 of this Example 2 (Genetic Condition Studies).

2. $M_3$ Plant Screen: In vitro $M_3$ plants from the four initial plant selections (labelled FS1, FS2, FS3 and FS4) are screened for PURSUIT™ resistance in vitro. $M_3$ seeds from each mature infloresence of these initial $M_2$ mutants are disinfested in 70% EtOH for 30 seconds followed by disinfestation in 50% solution containing 2.625% sodium hypochlorite (as described above) for 20 minutes under vaccuum with gentle agitation provided by a stir plate. The seeds are soaked in sterile distilled water in 100×5 mm sterile plastic petri dishes for 20–24 hours after which the embryos are excised and cultured onto medium containing either $10^{-4}$, $10^{-5}$, or $10^{-6}$ M PURSUIT™. Controls include non-mutagenized (Fidel) embryos cultured on medium with and without herbicide and $M_3$ material on medium without herbicide. Embryo ratings are taken at either two and one-half or three weeks after culture initiation.

None of the embryos (Fidel controls or $M_3$) cultured on medium containing $10^{-4}$ M PURSUIT™ germinates, although some of the $M_3$ embryos exhibit a small amount of primary root elongation (1–5 mm). $M_3$ embryos are somewhat tolerant to PURSUIT™ in the medium at a concentration of $10^{-5}$ M; however, there is still considerable growth inhibition. Table 2 presents the embryo ratings, "T"

(tolerant), "D" (damaged) and "S" (susceptible) for the embryos cultured on medium containing $10^{-5}$ and $10^{-6}$ M PURSUIT™.

Table 2: $M_3$ Plant Screen: Results of screening $M_3$ progeny of the four initial wheat selections in the in vitro seed screen. Embryo Ratings—"T"=Tolerant, "D"=Damaged, and "S"=Susceptible.

| Selection | Embryo Rating | | | Ave. Shoot Height (cm) | Range Shoot Heights (cm) |
|---|---|---|---|---|---|
| | T | D | S | | |
| PURSUIT™ Concentration = $10^{-5}$ | | | | | |
| FS1 | 21 | 16 | 42 | — | 0–1.5 |
| FS2 | 21 | 14 | 45 | — | 0–3.5 |
| FS3 | 12 | 9 | 58 | — | 0–4.5 |
| FS4 | 16 | 15 | 31 | — | 0–3.0 |
| Control 1 | 60 | 0 | 0 | 15.6 | 1–28 |
| Control 2 | 0 | 0 | 30 | — | — |
| Control $M_3$ | 27 | 1 | 1 | 14.7 | 1–28 |
| PURSUIT™ Concentration = $10^{-6}$ | | | | | |
| FS1 | 70 | 0 | 0 | 9.1 | 1–22 |
| FS2 | 64 | 1 | 0 | 11.4 | 1–23 |
| FS3 | 34 | 12 | 22 | 5.2 | 1–23 |
| FS4 | 59 | 8 | 13 | 13.4 | 1–33 |
| Control 1 | 20 | 0 | 0 | 23.1 | 14–32 |
| Control 2 | 0 | 0 | 15 | — | — |
| Control $M_3$ | 15 | 0 | 0 | 14.6 | 2–28 |

Control 1=Susceptible wheat seed (Fidel) on medium without herbicide. Control 2=Susceptible wheat seed (Fidel) on medium with herbicide. Control $M_3$=$M_3$ seed from the initial selections on medium with herbicide.

Based on these in vitro data, the mutant selections exhibit between 10- and 100-fold increased tolerance to PURSUIT™.

3. Segregation Study

A study is performed to assay $M_4$ progeny of the initial mutant wheat selections for imidazolinone resistance and homogeneity. $M_4$ seeds, from $M_3$ plants (derived from initial selections, FS1–FS4) which survive the two-step screen described previously, are used in this study. In addition, $M_4$ seeds derived from $M_3$ plants of each selection which are not screened (designated "stock" plants) are evaluated as well as Fidel controls. Seeds, derived from both stock and screened $M_3$ plants representing each infloresence of each original wheat selection (FS1–FS4), are planted in flats at a rate of twenty-five seeds per row and eight rows per flat. One week after planting, when the seedlings are at Z12 (two leaf) stage, the plants are sprayed with 62.5 g/ha PURSUIT™. The herbicide is applied with a laboratory belt sprayer at a rate of 950 L/ha with a belt speed of 12.5 sec/rev. using sprayer nozzle #40015E at a height 18 inches above the plants. Tween 20™ is used as a surfactant at 0.25% v/v. Plants are evaluated three weeks after spraying.

Fidel is completely susceptible to 62.5 g/ha PURSUIT™ (all of these plants die). The imidazoli-none-resistant winter wheat selections display excellent tolerance to the postemergent application of PURSUIT™ at 62.5 g/ha in this greenhouse evaluation. The progenies derived from selections FS1, FS2, and FS4 appear homogeneously resistant to PURSUIT™, even though a few susceptible plants and progenies with poor germination are observed. These three selections appear to be homozygous for resistance. The progenies from FS3 can be all susceptible, segregating or all resistant. Of segregating progenies with good germination, approximately one-fourth of the individuals are susceptible. This selection is apparently heterozygous, and requires an additional selfing generation to obtain uniformly homozygous material. Seed increase plots for all progenies are planted in the field. Following this greenhouse test, nonsegregating progenies derived from each individual selection are bulked to provide sufficient seed for a field tolerance test (Field Trial I, part 1 of Example 4).

4. Genetic Condition Studies

In order to determine whether the mutant wheat selections are allelic (and possibly derived from the same mutation) or different, the mutants need to be intercrossed. Also, resistant lines have to be crossed with susceptibles (Fidel) to establish the inheritance pattern for the resistance trait. With this is mind, all possible crosses and their reciprocals are made between five parental lines, Fidel, FS1, FS2, FS3 and FS4. The $F_1$ hybrids which result from these crosses are checked for resistance, selfed and test-crossed back to the susceptible parents in order to produce the necessary progenies to determine inheritance and allelism information for the selections.

Experiment 1: Six flats containing Metro Mix 350™ are planted with $F_1$ hybrids derived from each of the following crosses: FS1×Fidel: FS2×Fidel; FS3×Fidel; FS4×Fidel and Fidel (susceptible, parental cultivar). One week later, the flats are sprayed, one flat per herbicide rate, with PURSUIT™ at 50, 100, 150, 200, and 250 g/ha to determine the genetic condition of the herbicide resistant trait in the selections, FS1–FS4. The herbicide is applied with a laboratory belt sprayer at a rate of 950 L/ha with a belt speed of 12.5 sec/rev using sprayer nozzle #40015E. Tween $_{20}$™ is used as the surfactant at 0.25% v/v in the herbicide solutions. Plants are rated 10 days after herbicide treatment.

The hybrids are stunted but not killed at 250 g/ha PURSUIT™, indicating that even in the heterozygous condition, these plants express relatively high levels of resistance to the imidazolinones. Fidel is killed at a rate of 150 g/ha PURSUIT™ and is severely injured at rates of 50 and 100 g/ha. The hybrids, FS$_1$×Fidel, FS2×Fidel, FS3× Fidel, and FS4×Fidel, all express herbicide resistance in the $F_1$ generation. A segregation ratio of 1 resistant: 1 susceptible would suggest a heterozygous condition. However, this is not observed in any of the four selections. Based on these data, the gene conferring herbicide resistance in the resistant wheat mutants is dominant and homozygous.

Experiment 2: This experiment continues the evaluation of the mutant wheat selections by examining herbicide resistance in reciprocal crossed and selfed material. Reciprocal crosses are made between $M_3$ plants representing each of the original four mutant selections and between these selections and Fidel. Progeny of these crosses as well as selfed progeny of the plants used in the crosses are planted in 6 inch azalea pots in Metro Mix 350™. Ten pots of each cross are planted with two seeds planted per pot. Ten days later, all of the selfed and reciprocally crossed progeny are sprayed postemergence with PURSUIT™ at 200 g/ha. Herbicide treatment is applied as described in Experiment 1. Plants are thinned to one plant per pot (by removing the weaker of the two plants per pot) one week after herbicide treatment. There is 100% germination of seed from the mutant reciprocal crosses and greater than 90% germination of seed from the selfed mutants. None of the mutant crosses is damaged by the PURSUIT™ challenge.

Experiment 3: Testcrosses of the $F_1$ hybrids (described in Experiment 1) back to Fidel are sprayed with 200 g/ha of PURSUIT™. The following testcrosses are planted in 6 inch azalea pots in Metro Mix 350™. The number of pots planted per cross is indicated by the number after the cross:

| | | |
|---|---|---|
| Fidel × (Fidel/FS1) | | 12 |
| Fidel × (Fidel/FS2) | | 21 |
| Fidel × (Fidel/FS3) | | 9 |
| Fidel × (Fidel/FS4) | | 8 |
| Fidel* | | 20 |

(*There are two plantings of Fidel of twenty pots each.)

Approximately one month later, the plants are sprayed (except for Fidel). PURSUIT™ (200 g/ha) is applied as previously described. The plants are rated three and one-half weeks later.

Out of 49 test-cross progeny sprayed, 29 survive and 20 are killed. The 29:20 segregation approximates the 1:1 segregation expected if a single dominant (or semidominant) gene controls the inheritance. However, the putative heterozygotes in this study are damaged considerably more than plants sprayed with the same rate of herbicide in a previous study. It is unclear whether treatment at a later growth stage causes the increased damage to the heterozygotes, or whether other factors are involved.

Experiment 4: The resistant wheat selections, FS1–FS4, are crossed to Fidel and the $F_1$ seed from these crosses is selfed. The crosses are as follows:

(Fidel×FS1) selfed
(Fidel×FS2) selfed
(Fidel×FS3) selfed
(Fidel×FS4) selfed

The $F_2$ progeny from these crosses and their susceptible progenitor variety Fidel are planted in flats. Five $F_2$ progenies are used for each of the four crosses. One flat is planted of each progeny for each cross. The flats consist of six rows per flat with 25 seeds per row. The flats are sprayed postemergence with 200 g/ha PURSUIT™ eleven days later. The PURSUIT™ is applied as previously described.

This rate of PURSUIT™ is determined to be lethal to susceptible wheat, yet non-lethal to plants heterozygous or homozygous for resistance. Segregation for herbicide resistance in this progeny confirm that the resistance trait for each of the four selections (FS1–FS4) is inherited as a single dominant or semi-dominant trait. $F_2$ progenies of each of the four crosses give clean ratios of 3 (resistant): 1 (susceptible) when sprayed postemergence with 200 g/ha PURSUIT™.

Experiment 5: Crosses and reciprocal crosses are made between the four mutant wheat selections. The $F_1$ seed from these crosses is planted and the plants allowed to self. The $F_2$ seed is harvested and used in this experiment to determine allelism of the four selections. Whole-flats are filled with Metro Mix 350™ and are sown with 100 seeds per cross (four rows with 25 seeds/row). In addition a row of susceptible Fidel is sown in each flat. Three sources from each cross are used. When the seedlings reach the Z12 stage, the flats are sprayed with PURSUIT™ at 200 g/ha. The PURSUIT™ solution is applied as previously described. Four weeks after treatment the number of resistant versus the number of susceptible plants is determined.

Allelism studies between the four resistant wheat selections demonstrate that all the selections are allelic or very tightly linked. Few or no susceptible segregants are observed in the $F_2$ generation of intercross hybrids between the selections. In the event that the genes are nonallelic and unlinked, the $F_2$ progenies are expected to segregate in a 15 (resistant): 1 (susceptible) ratio. Table 3 presents the results of these genetic condition studies.

Table 3: Genetic Condition Studies: Number of Plants which are resistant/susceptible to 200 g/ha PURSUIT™.

Data taken three weeks after treatment.

| Source | Resist | Suscept | Source | Resist | Suscept |
|---|---|---|---|---|---|
| (FS1/FS2)X-1 | 71 | 1 | (FS2/FS1)X-1 | 95 | 0 |
| (FS1/FS2)X-2 | 85 | 2 | (FS2/FS1)X-2 | 91 | 0 |
| (FS1/FS2)X-3 | 74 | 1 | (FS2/FS1)X-3 | 97 | 0 |
| Total | 230 | 4 | Total | 283 | 0 |
| (FS1/FS3)X-1 | 82 | 0 | (FS3/FS1)X-2 | 95 | 0 |
| (FS1/FS3)X-2 | 92 | 0 | (FS3/FS1)X-3 | 97 | 0 |
| (FS1/FS3)X-3 | 93 | 0 | (FS3/FS1)X-5 | 94 | 1 |
| Total | 267 | 0 | Total | 286 | 1 |
| (FS1/FS4)X-1 | 96 | 0 | (FS4/FS1)X-1 | 93 | 1 |
| (FS1/FS4)X-2 | 90 | 0 | (FS4/FS1)X-2 | 91 | 0 |
| (FS1/FS4)X-3 | 93 | 2 | (FS4/FS1)X-3 | 94 | 1 |
| Total | 279 | 2 | Total | 278 | 2 |
| (FS2/FS3)X-1 | 99 | 0 | (FS3/FS2)X-1 | 96 | 0 |
| (FS2/FS3)X-2 | 87 | 1 | (FS3/FS2)X-2 | 94 | 0 |
| (FS2/FS3)X-3 | 92 | 0 | (FS3/FS2)X-3 | 96 | 0 |
| Total | 278 | 1 | Total | 286 | 0 |
| (FS2/FS4)X-1 | 102 | 0 | (FS4/FS2)X-1 | 94 | 0 |
| (FS2/FS4)X-2 | 97 | 0 | (FS4/FS2)X-2 | 95 | 1 |
| (FS2/FS4)x 3 | 97 | 1 | (FS4/FS2)X-3 | 95 | 0 |
| Total | 296 | 1 | Total | 284 | 1 |
| (FS3/FS4)X-1 | 98 | 0 | (FS4/FS3)X-1 | 96 | 0 |
| (FS3/FS4)X-2 | 96 | 0 | (FS4/FS3)X-2 | 100 | 0 |
| (FS3/FS4)X-3 | 96 | 0 | (FS4/FS3)X-3 | 94 | 0 |
| Total | 290 | 0 | Total | 290 | 0 |

In no case does the number of susceptible segregants approach 1/16th of the total (Table 3). Also, no maternal effects on inheritance are observed. These data support the likelihood that all four selections are derived from the same mutational event or are very tightly linked.

Experiment 6: Seeds from selfed progeny from the second backcross of the resistant mutants to Fidel (susceptible progenitor cultivar) are planted in standard flats filled with Metro Mix 350™. Thirty seeds are planted per source. Seven to ten days after planting, these flats are sprayed with 200 g/ha PURSUIT™ applied as previously described. Three weeks after treatment, the plants are evaluated for segregation of the resistance trait. As expected, some progeny are completely resistant, some progeny are segregating for resistance, i.e., some progeny are resistant and some progeny are susceptible, while other progeny are completely susceptible to herbicide. Homozygous resistant plants are selected and used to increase seed quantities (in the nursery) for the improved resistant cultivar.

EXAMPLE 3

Herbicide Resistance Studies

1. Level and Spectrum of Herbicide Resistance

This greenhouse test examines the level and spectrum of herbicide resistance of the mutant selections at the whole plant level. Four imidazolinones (PURSUIT™, SCEPTER™, ARSENAL™ and Compound 2 and one sulfonylurea (OUST™, a registered trademark of E.I. du Pont de Nemours and Company, which is the methyl ester of o-[[3-(4,6-dimethylpyrimidin-2-yl)ureido]sulfonyl]-benzoic acid) are tested. Compound 2 is a potential short residual imidazolinone and is 2-(4-isopropyl-4-methyl-5-oxo-2-imidazolin-2-yl)-5-(methoxymethyl)-nicotinic acid. Growth rates, as determined by plant height, of treated plants are compared to untreated controls. $M_4$ seed, derived from $M_3$ plants screened for herbicide resistance using the two-step screen (seed soak and spray) and unscreened $M_3$ stock plants, are bulked after they are shown to be non-segregating (see Segregation Study). These lines are bulked according to their parental lines: FS1, FS2, FS3 and FS4. Fidel (wild-type) is used is a control and for performance comparison purposes. Five seeds from each of these lines (including Fidel) are planted per pot in six inch Azalea pots and are later thinned to three plants per pot. Three replicates are used per treatment (chemical and rate) for each line, and six replicates per wheat line are used as untreated controls. Plants are sprayed postemergence, 10 days after planting, with the following herbicides and rates:

| Imidazolinones: | | |
|---|---|---|
| PURSUIT ™ | 20, 40, 80, 160, 320 | g/ha |
| SCEPTER ™ | 40, 80, 160, 320, 640 | g/ha |
| ARSENAL ™ | 3, 6, 12, 24, 48 | g/ha |
| Compound 2 | 20, 40, 80, 160, 320 | g/ha |
| Sulfonylurea | | |
| OUST ™ | 5, 10, 20, 40, 80 | g/ha |

(*Note: Plants sprayed with ARSENAL ™ are planted three days prior to the plants in the other treatments; however, measurements are taken with the other treatments. In addition, although there are three replicates per ARSENAL ™ rate evaluated, there are only two plants per pot rather than three.)

Tween 20™ is added at 0.25% v/v to the herbicide solutions prior to spraying. The herbicides are applied with a laboratory belt sprayer at a rate of 400 L/ha at a distance 18 inches above the wheat plants with a belt speed of 8.2 sec/rev and sprayer nozzle #65015E. Plant height is measured immediately prior to spraying and at one week intervals for four weeks.

The four selections are similar in both their spectrum and level of resistance. FS3 is slightly less resistant than the other three selections. Since FS3 is selected as a heterozygote, heterozygous or susceptible individuals may be inadvertently included during bulking of the seed to conduct these experiments. Based on plant growth four weeks after treatment, the mutant wheat is resistant to more than 320 g/ha PURSUIT™, more than 640 g/ha SCEPTER™, more than 48 g/ha ARSENAL™, more than 80 g/ha Compound 2, and more than 5 g/ha OUST™. These numbers translate approximately to an 8-fold increased tolerance to PURSUIT™, more than a 16-fold inceased tolerance to SCEPTER™ and ARSENAL™, a 16-fold increase in tolerance to Compound 2, and a 2-fold increase tolerance to OUST™. FIGS. 7–10a demonstrate this tolerance for one of the mutant wheat selections (FS1) to ARSENAL™, OUST™, PURSUIT™, SCEPTER™, and Compound 2, respectively.

2. Preemeraence Herbicide Tolerance

In this study the imidazolinones, SCEPTER™, PURSUIT™, ARSENAL™, and Compound 2, and the sulfonyl-urea, OUST™, are applied pre-emergence (rather than postemergence as described in part 1 of this Example 3) to the wheat variety Fidel and the resistant selections FS2 and FS4 to evaluate herbicide tolerance.

$M_4$ seed of two of the mutant selections, FS2 and FS4, and seed of the susceptible variety Fidel is used in this experiment. Five seeds from each wheat line are planted per pot in Sassafras (sandy loam) soil in six inch Azalea pots. Four replicates are used per treatment (chemical & rate) for each line, and six replicates per wheat line are used as untreated controls. The day after the seeds are planted, the pots are sprayed with the following herbicides and rates:

| PURSUIT ™ | 40, 80, 160, 320, 640 | g/ha |
|---|---|---|
| SCEPTER ™ | 40, 80, 160, 320, 640 | g/ha |
| ARSENAL ™ | 2.5, 5, 10, 20, 40 | g/ha |
| Compound 2 | 5, 10, 20, 40, 80 | g/ha |
| OUST ™ | 5, 10, 20, 40, 80 | g/ha |

The herbicides are applied as described above (Level and Spectrum of Herbicide Resistance). The pots are watered after spraying. Plant heights are measured at four weeks after treatment.

Figure 11:
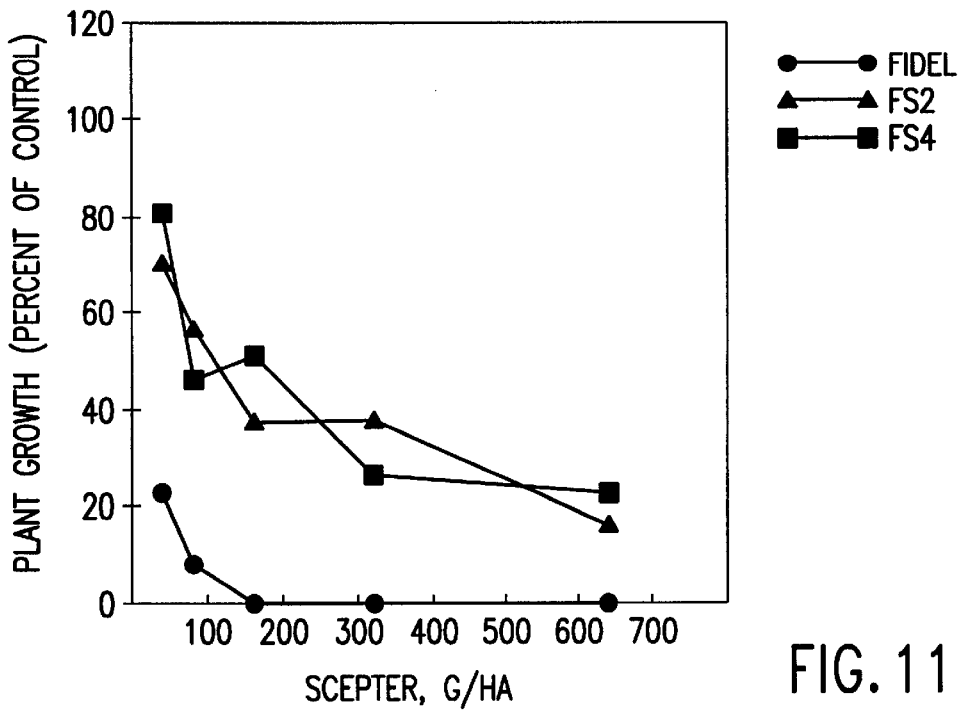
FIG. 11 depicts a comparison of growth (as a percentage of control plants) of wild-type wheat (Fidel) versus the $M_4$ wheat mutants from FS2 and FS4 four weeks after pre-emergent treatment with SCEPTER™.
Figure 12:
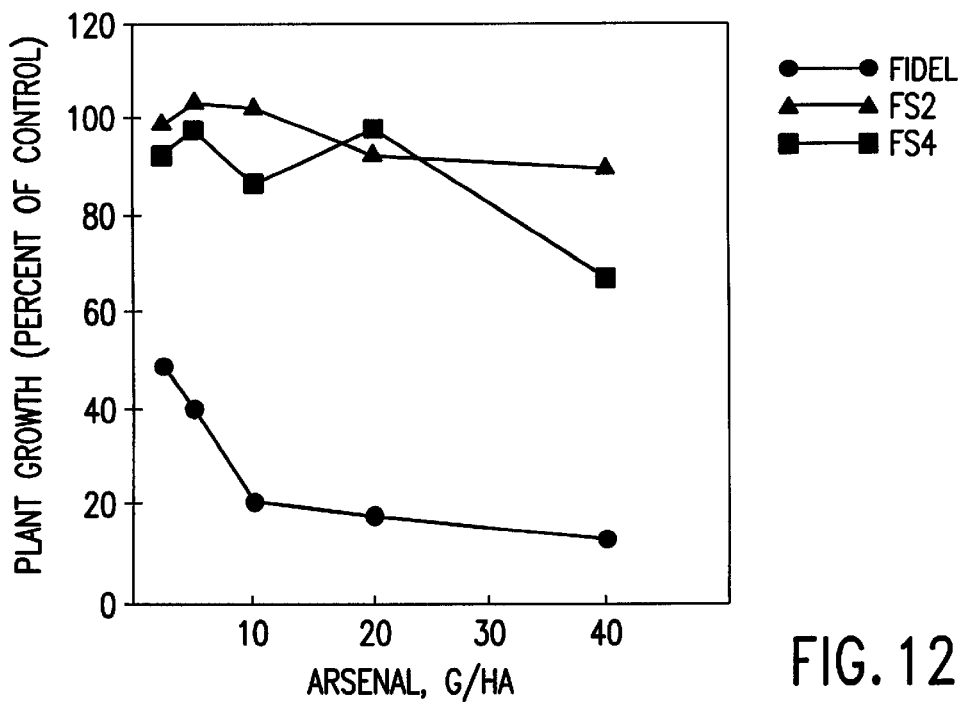
FIG. 12 depicts a comparison of growth (as a percentage of control plants) of wild-type wheat (Fidel) versus the $M_4$ wheat mutants from FS2 and FS4 four weeks after pre-emergent treatment with ARSENAL™.
Figure 13:
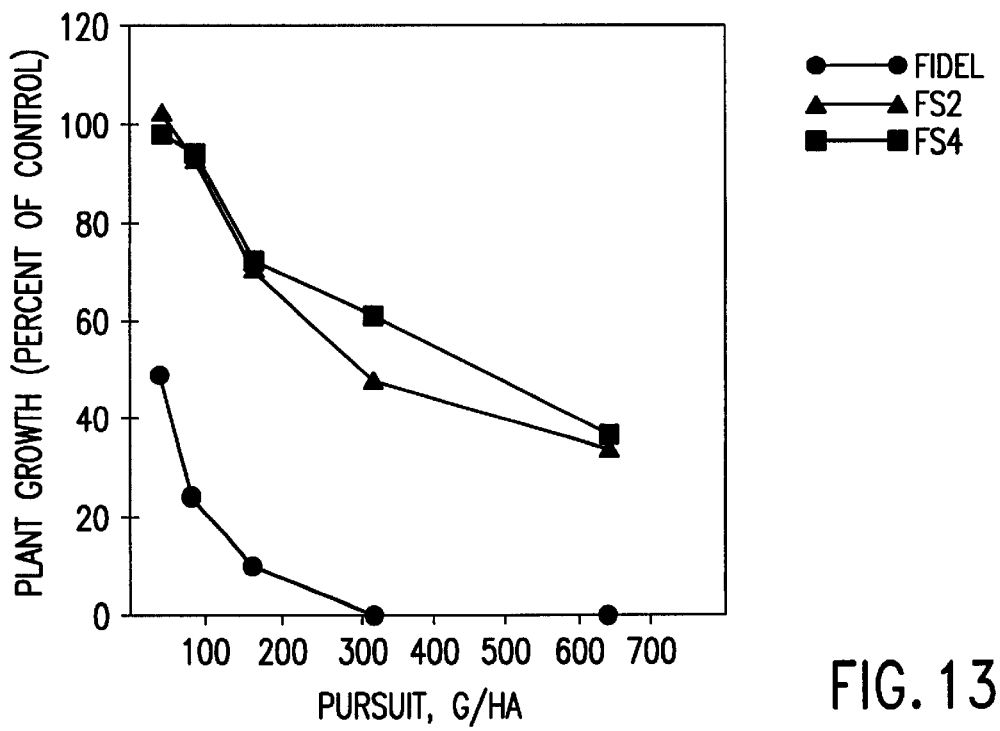
FIG. 13 depicts a comparison of growth (as a percentage of control plants) of wild-type wheat (Fidel) versus the $M_4$ wheat mutants from FS2 and FS4 four weeks after pre-emergent treatment with PURSUIT™.
Figure 14:
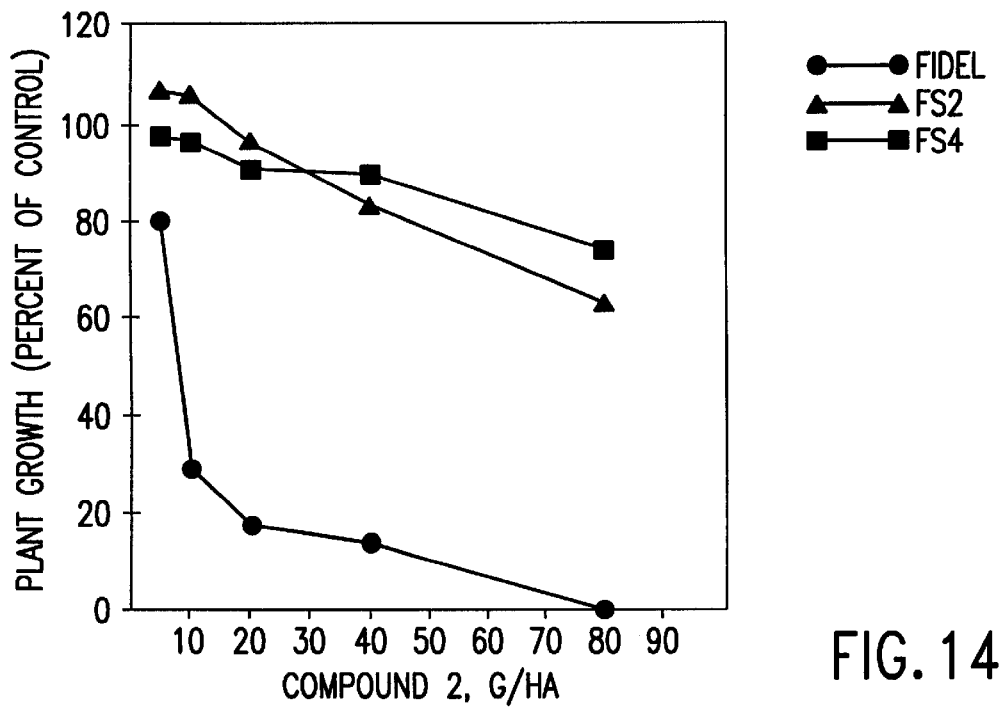
FIG. 14 depicts a comparison of growth (as a percentage of control plants) of wild type wheat (Fidel) versus the $M_4$ wheat mutants from FS2 and FS4 four weeks after pre-emergent treatment with an imidazolinone herbicide, Compound 2.

Based on plant growth after four weeks, the selections FS2 and FS4 have an approximately 8-fold increased tolerance to ARSENAL™ and PURSUIT™ (FIGS. 12 and 13, respectively), an 8- to 16-fold increased tolerance for Compound 2 (FIG. 14) and SCEPTER™ (FIG. 11). The increase in tolerance to OUST™ appears to be 2- to 4-fold. Similar results are observed for root and shoot fresh weight data measured seven weeks after treatment.

3. Postemergence Herbicide Tolerance

In this second greenhouse test, the upper limits of the mutant selections' resistance to postemergent applications of PURSUIT™ and Compound 2 are examined. $M_4$ seed of two of the mutant selections, FS2 and FS4, and seed of Fidel are used in this experiment. Five seeds from each line are planted per pot in sterile Metro Mix 350™ in six inch Azalea pots. Immediately prior to herbicide treatment, these plants are thinned to three plants per pot. Three replicates are used per treatment (chemical & rate) for each line, and six replicates per wheat line are used as untreated controls. The plants are sprayed postemergence, 10 days after planting, with the following herbicides and rates (g/ha):

| PURSUIT ™: | 10, 25, 50, 100, 250, 500, 1000, 2500 |
|---|---|
| Compound 2: | 2.5, 5, 10, 25, 50, 100, 250, 500 |

The herbicides are applied as previously described. Plant height is measured immediately prior to spraying. Plant heights are also measured at two and four weeks after treatment, and shoot fresh weights measured at seven weeks after treatment.

Figure 15:
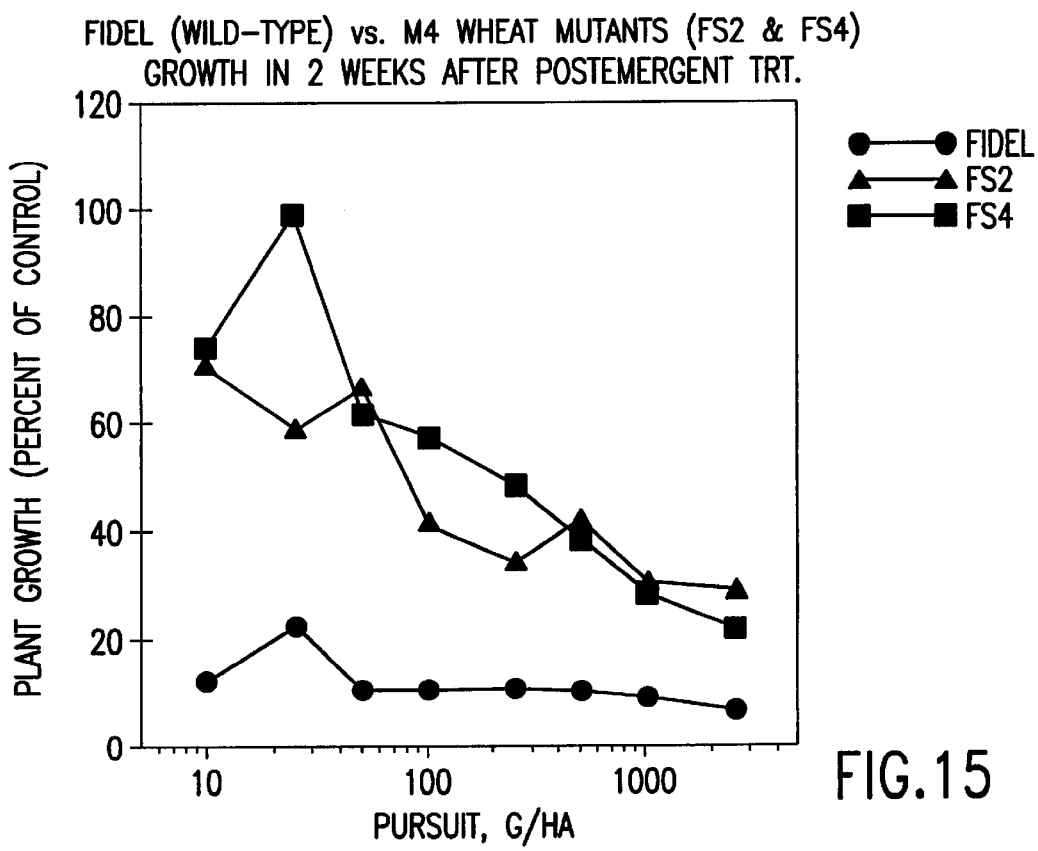
FIG. 15 depicts a comparison of growth (as a percentage of control plants) of wild-type wheat (Fidel) versus the $M_4$ wheat mutants from FS2 and FS4 two weeks after post-emergence treatment with PURSUIT™.
Figure 16:
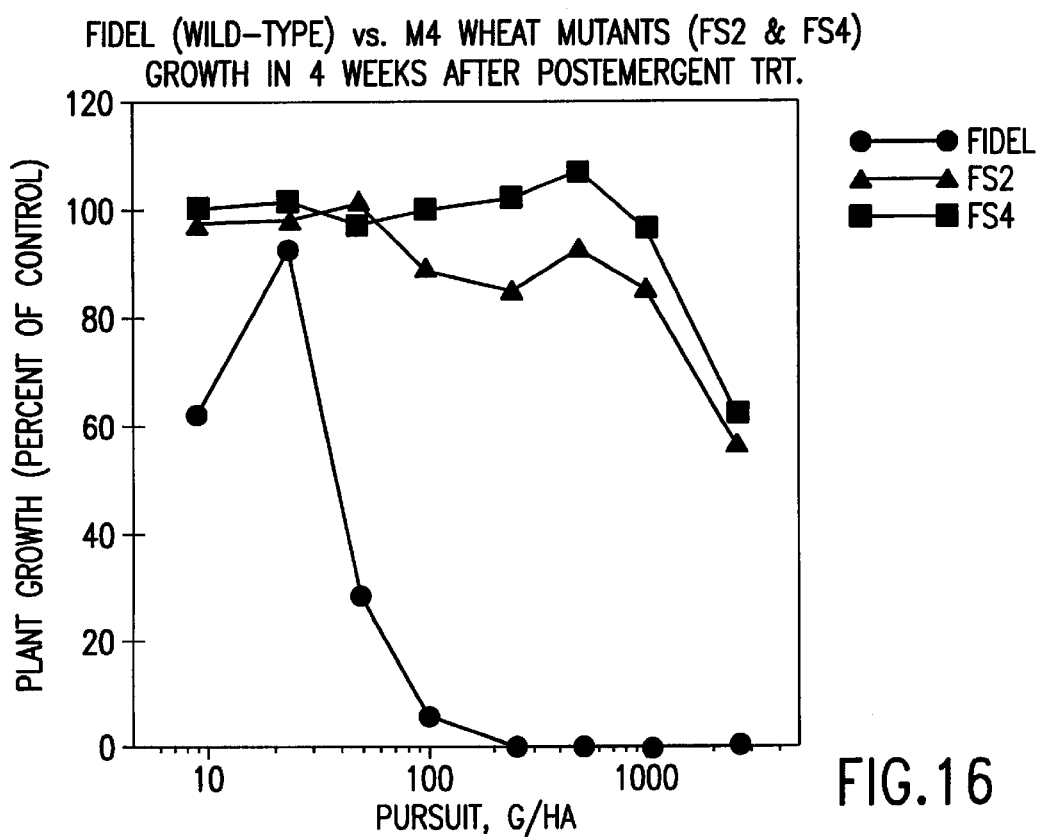
FIG. 16 depicts a comparison of growth (as a percentage of control plants) of wild-type wheat (Fidel) versus the $M_4$ wheat mutants from FS2 and FS4 four weeks after post-emergence treatment with PURSUIT™.
Figure 17:
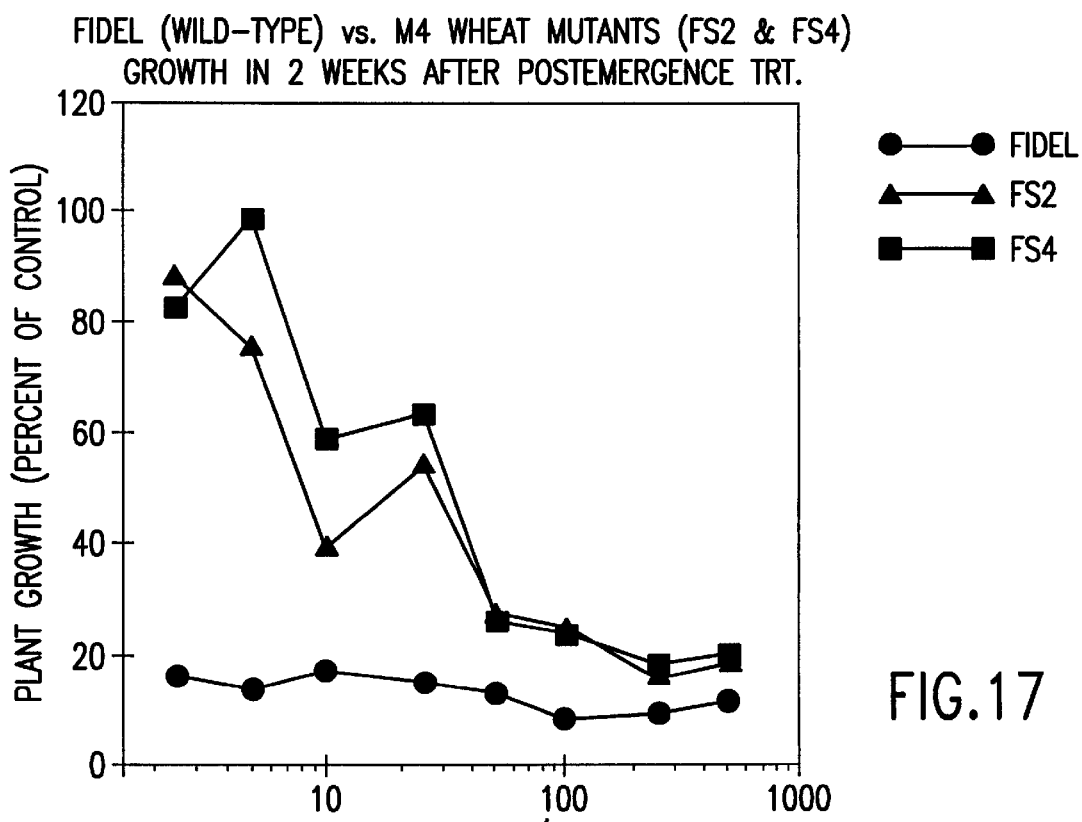
FIG. 17 depicts a comparison of growth (as a percentage of control plants) of wild-type wheat (Fidel) versus the $M_4$ wheat mutants from FS2 and FS4 two weeks after post-emergence treatment with Compound 2.
Figure 18:
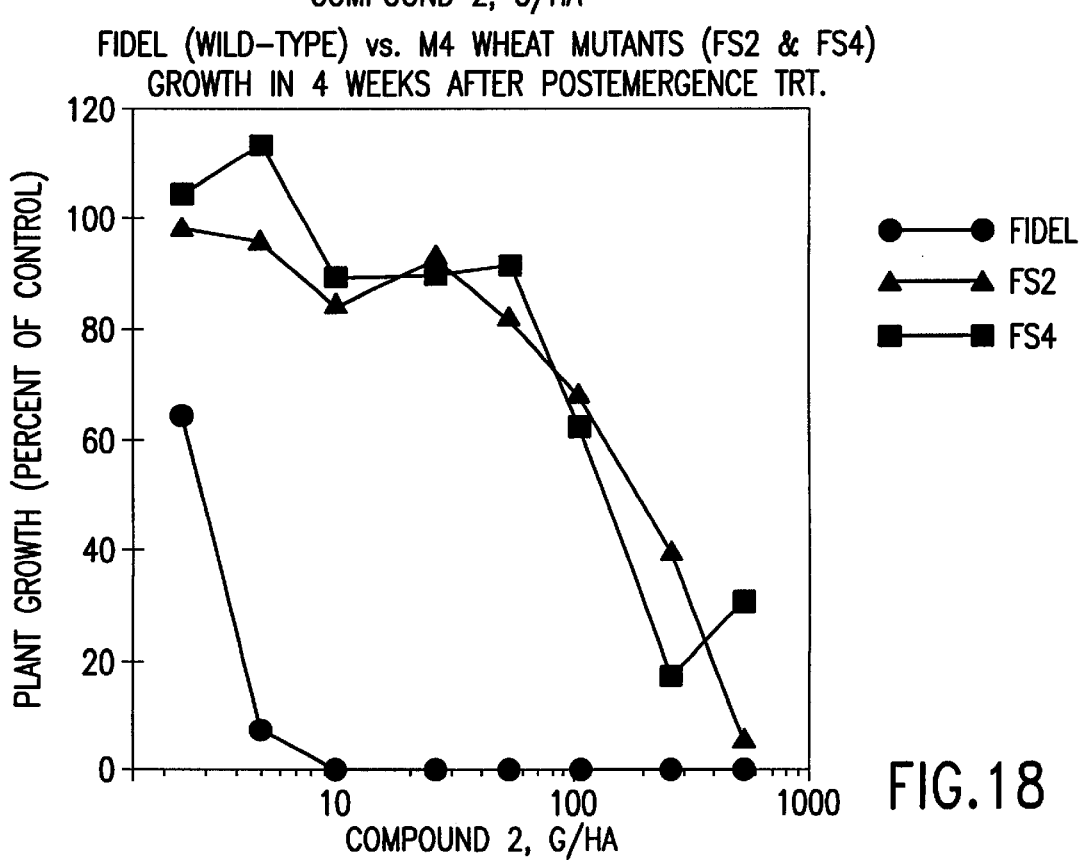
FIG. 18 depicts a comparison of growth (as a percentage of control plants) of wild-type wheat (Fidel) versus the $M_4$ wheat mutants from FS2 and FS4 four weeks after post-emergence treatment with Compound 2.
Figure 19:
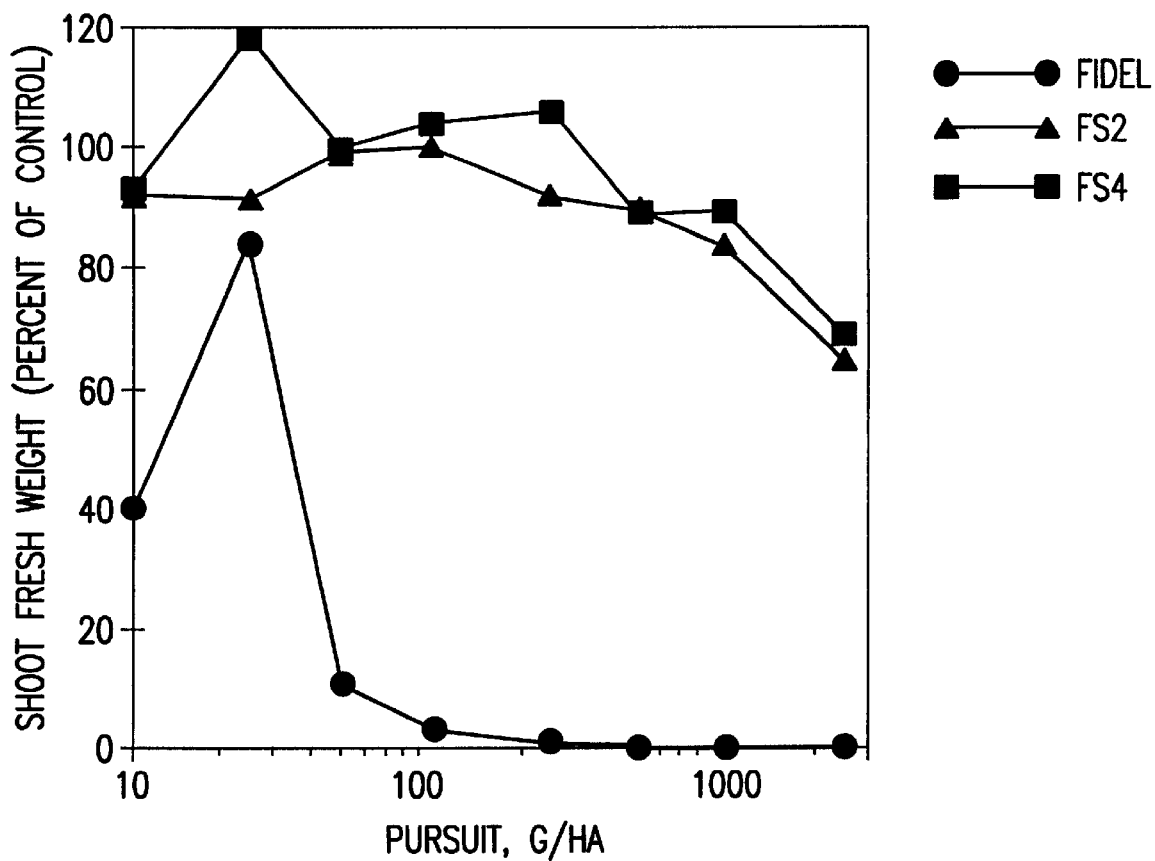
FIG. 19 depicts a comparison of shoot fresh weight (as a percentage of control plants) of wild-type wheat (Fidel) versus the $M_4$ wheat mutants from FS2 and FS4 seven weeks after post-emergence treatment with PURSUIT™.
Figure 20:
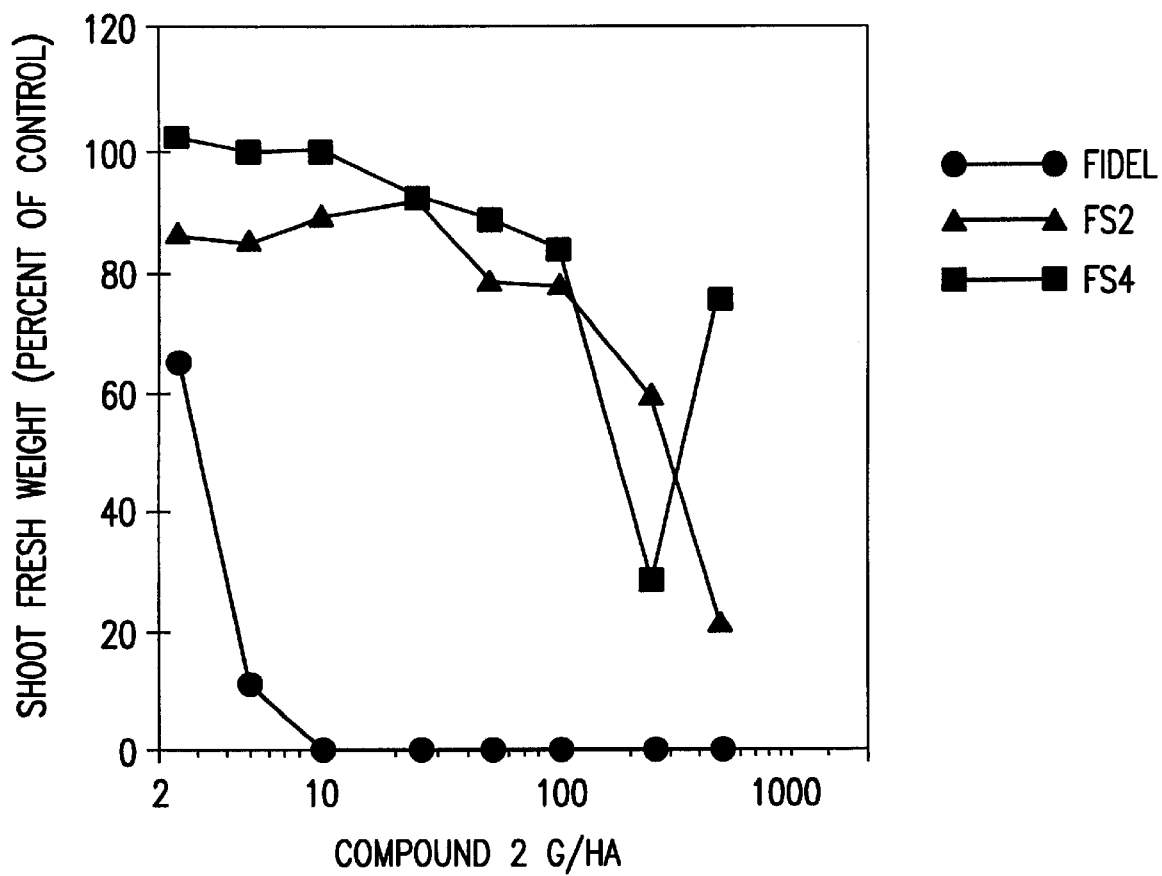
FIG. 20 depicts a comparison of shoot fresh weight (as a percentage of control plants) of wild-type wheat (Fidel) versus the $M_4$ wheat mutants from FS2 and FS4 seven weeks after post-emergence treatment with Compound 2.

The selections exhibit initial stunting symptoms at two weeks after treatment for all treatment combinations when compared to untreated controls (FIGS. 15 and 17). However, by four weeks after treatment, the FS2 and FS4 plant heights equal the untreated controls at rates up to 500–1000 g/ha PURSUIT™ (FIG. 16) and 25–50 g/ha Compound 2 (FIG. 18). The selections display a 40- to 100-fold increased tolerance to PURSUIT™ and Compound 2 applied postemergence in this test as compared to Fidel (unselected). Shoot fresh weight data taken seven weeks after treatment indicates that FS2 and FS4, at these same herbicide rates, have fresh weights equalling 90–100% of the untreated control fresh weights (FIGS. 19 and 20).

4. Sulfamoylurea Tolerance Premeraence

Two experiments are conducted to determine whether the imidazolinone resistant wheat selections express resistance to sulfamoylurea herbicides. Resistance to four sulfamoylurea herbicides (described below) and one sulfonylurea herbicide (OUST™) is tested in postemergence and preemergence tests.

In a first experiment, the mutant wheat selection, FS2, from bulked $M_3$–$M_4$ seed and Fidel seed, is planted in six inch Azalea pots in Sassafras (sandy loam) soil. Three seeds are planted per pot initially; these are subsequently thinned to two plants. There are three replicates of each treatment. In addition, the untreated controls consist of 15 replicates each of Fidel and FS2. Plants are sprayed preemergence with the following herbicides and rates:

| Sulfamoylureas: | | |
|---|---|---|
| Compound 3: | 12.5, 25, 50, 100, 200 | g/ha |
| Compound 4: | 62.5, 125, 250, 500, 1000 | g/ha |
| Compound 5: | 12.5, 25, 50, 100, 200 | g/ha |
| Compound 6: | 12.5, 25, 50, 100, 200 | g/ha |

Compound 3 is 1-(4-methoxy-6-methyl-s-triazin-2-yl)-3-[(o-propionylphenyl)sulfamoyl]urea, Compound 4 is 1-(4,6-dimethoxy-2-pyrimidinyl)-3-[(o-propionylphenyl)sulfamoyl]urea, Compound 5 is 1-[(o-acetylphenyl)sulfamoyl]-3-(4-methoxy-6-methyl-2-pyrimidinyl)urea, and Compound 6 is 1-[(o-acetylphenyl)sulfamoyl]-3-(4-methoxy-6-methyl-s-triazin-2-yl)urea. All four compounds are disclosed in U.S. Pat. No. 4,622,065.

Sulfonylurea:

OUST™: 1.56, 3.125, 6.25, 12.5, 25 g/ha

The herbicides are applied as previously described.

The pre-emergence study has very poor emergence, and again, no differences are observed visually between Fidel and the resistant selection.

5. Sulfamoylurea Tolerance Postemergence

In a second experiment, the mutant wheat selection, FS2, from bulked $M_3$–$M_4$ seed, and Fidel seed are planted in 6" Azalea pots in sterile Metro Mix 350™. Three seeds are planted per pot initially; these are subsequently thinned to two plants. There are three replicates of each treatment. In addition, the untreated controls consist of 15 replicates each of Fidel and FS2. Plants are sprayed postemergence, 12 days after planting, with the following herbicides and rates:

| Sulfamoylureas: | | |
|---|---|---|
| Compound 3: | 12.5, 25, 50, 100, 200 | g/ha |
| Compound 4: | 62.5, 125, 250, 500, 1000 | g/ha |
| Compound 5: | 12.5, 25, 50, 100, 200 | g/ha |
| Compound 6: | 12.5, 25, 50, 100, 200 | g/ha |
| Sulfonylurea: | | |
| OUST ™: | 6.25, 12.5, 25, 50, 100 | g/ha |

The herbicides are applied as previously described.

Resistant and susceptible wheat are treated with rates of the herbicides expected to cause severe damage or lethality to the susceptible wheat. Unfortunately, the susceptible wheat cultivar (Fidel) is not affected (as observed visually) even by the highest rates used for the sulfamoylurea herbicides tested in the postemergence test. Either Fidel wheat is relatively tolerant to the sulfamoylurea herbicides, the rates are not high enough to cause damage, or the herbicide does not damage the wheat for some other reason (formulation, environmental influence, etc.). The resistant wheat exhibit 2–4 fold increased tolerance to OUST™ in this study; these results are similar to results from previous experiments.

6. $M_3$–$M_4$ Wheat Herbicide Resistance Spectrum

In this experiment, the tolerance of imidazolinone-resistant wheat to three sulfonylurea herbicides (BEACON™, CLASSIC™ and OUST™ (BEACON™ is a registered trademark of Ciba-Geigy and is 2-[4,6-bis-(difluoro-methoxy)-pyrimidin-2-ylcarbamoylsulfamoyl] benzoic acid; CLASSIC™ is a registered trademark of E.I. du Pont de Nemours and Company and is the ethyl ester of o-[[(4-chloro-6-methoxy-2-pyrimidinyl)-carbamoyl]-sulfamoyl]-benzoic acid), a sulfamoylurea herbicide (Compound 3), a sulfonylcarboxamide (Compound 1), and an imidazolinone herbicide (Compound 7, which is 3-(4-isopropyl-4-methyl-5-oxo-2-imidazolin-2-yl)-2-methyl-crotonic acid), is examined to look for cross-tolerance to AHAS-inhibiting herbicides other than the imidazolinones. The mutant wheat selection, FS2, from bulked $M_3$–$M_4$ seed, and Fidel seed are planted in 5" Azalea pots in sterile Metro Mix 350™. Three seeds are planted per pot initially; these are subsequently thinned to two plants. Each treatment consists of three replicates. In addition, there are six replicates each of FS2 and Fidel which are used as untreated controls. Plants are sprayed postemergence, 7 days after planting, with the following herbicides and rates:

| Sulfonylureas: | | |
|---|---|---|
| BEACON ™: | 15.6, 31.3, 62.5, 125, 25.0 | g/ha |
| CLASSIC ™: | 31.3, 62.5, 125, 250, 500 | g/ha |
| OUST ™: | 6.25, 12.5, 25, 50, 100 | g/ha |
| Sulfamoylurea: | | |
| Compound 3: | 125, 250, 500, 1000, 2000 | g/ha |
| Sulfonylcarboxamide: | | |
| Compound 1: | 250, 500, 1000, 2000, 4000 | g/ha |
| Imidazolinone: | | |
| Compound 7: | 187.5, 375, 750 | g/ha |

The herbicides are applied as previously described. Plants are rated at two, three and four weeks after treatment with herbicide.

Figure 21:
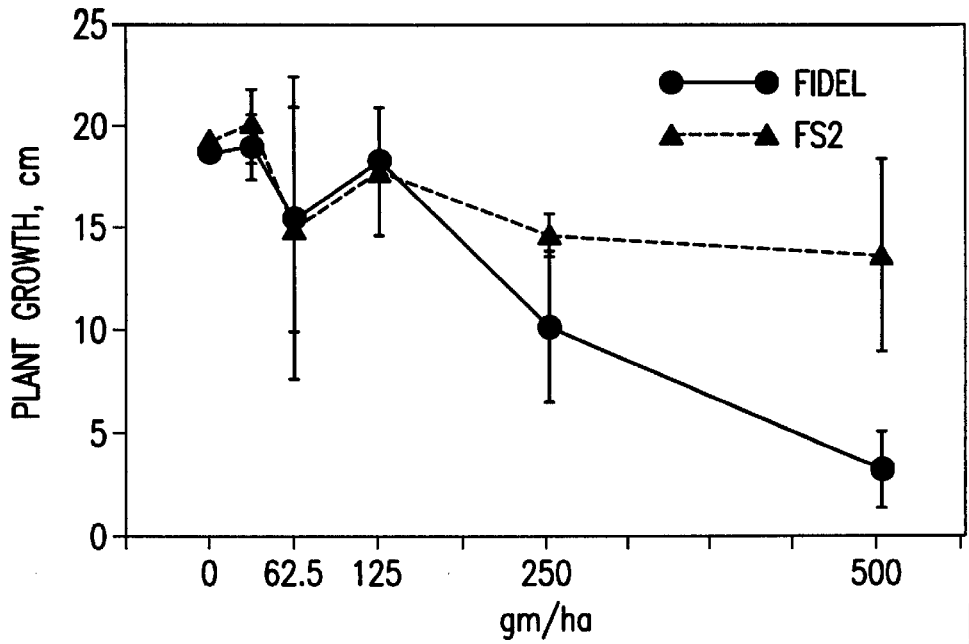
FIG. 21 depicts a comparison of plant growth (in cm.) of wild-type wheat (Fidel) versus the FS2 mutant from bulked $M_3$–$M_4$ seed four weeks after post-emergence treatment with CLASSIC™.
Figure 22:
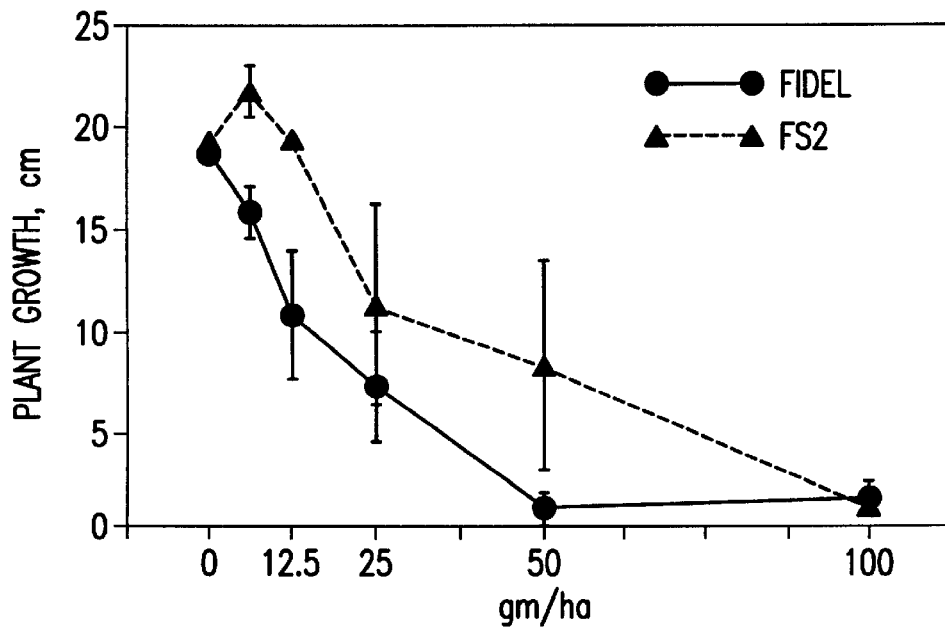
FIG. 22 depicts a comparison of plant growth (in cm.) of wild-type wheat (Fidel) versus the FS2 mutant from bulked $M_3$–$M_4$ seed four weeks after post-emergence treatment with a sulfonylurea herbicide, OUST™.
Figure 23:
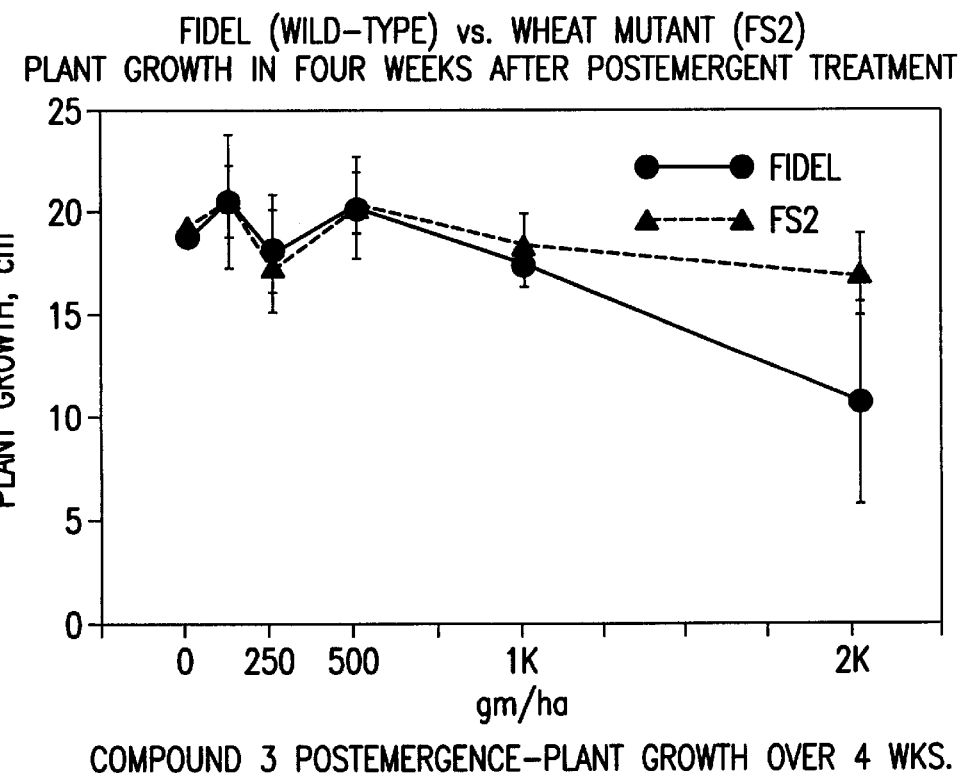
FIG. 23 depicts a comparison of plant growth (in cm.) of wild-type wheat (Fidel) versus the $F_2$ mutant from bulked $M_3$–$M_4$ seed four weeks after post-emergence treatment with a sulfamoylurea herbicide, Compound 3.
Figure 24:
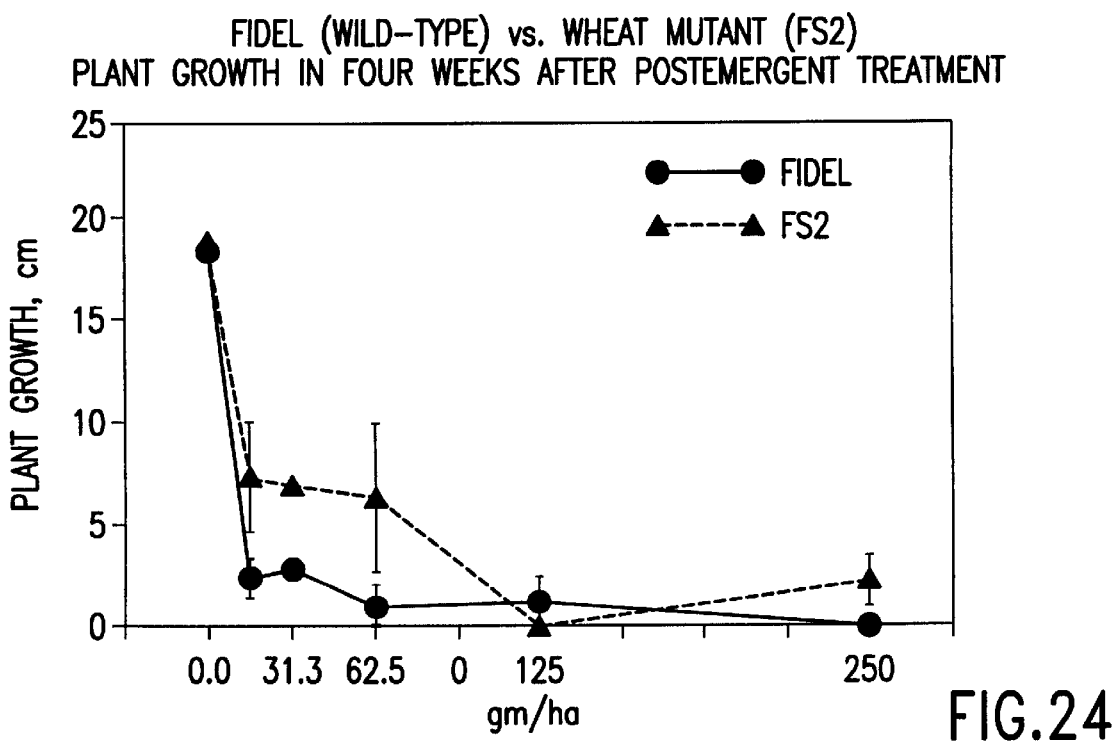
FIG. 24 depicts a comparison of plant growth (in cm.) of wild-type wheat (Fidel) versus the $F_2$ mutant from bulked $M_3$–$M_4$ seed four weeks after post-emergence treatment with a sulfonylurea herbicide, BEACON™.
Figure 25:
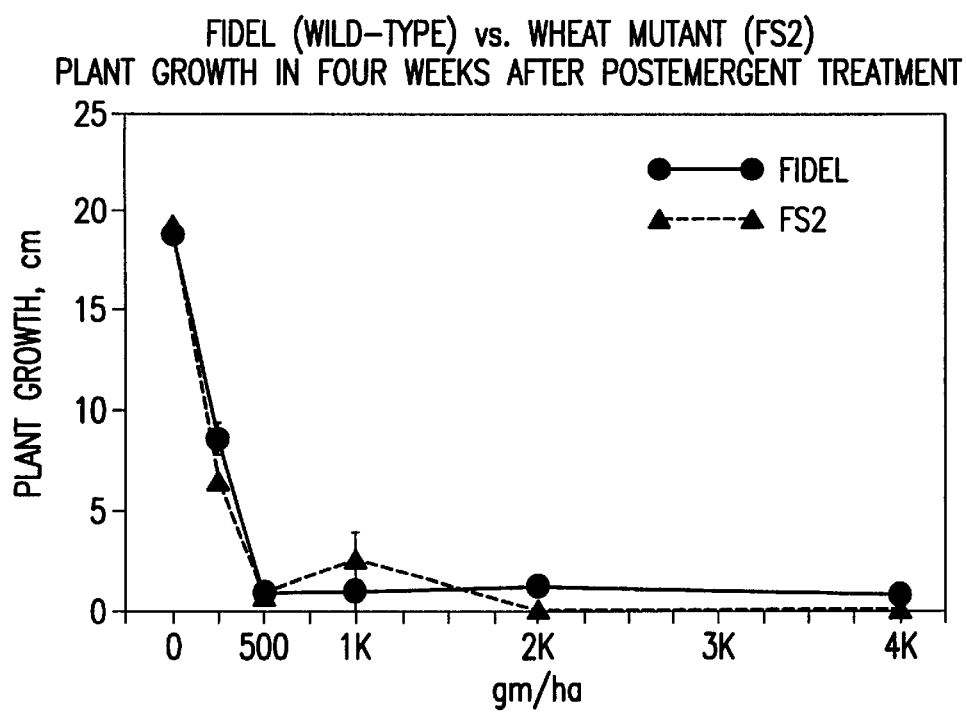
FIG. 25 depicts a comparison of plant growth (in cm.) of wild-type wheat (Fidel) versus the $F_2$ mutant from bulked $M_3$–$M_4$ seed four weeks after post-emergence treatment with a sulfonylcarboxamide herbicide, Compound 1.
Figure 26:
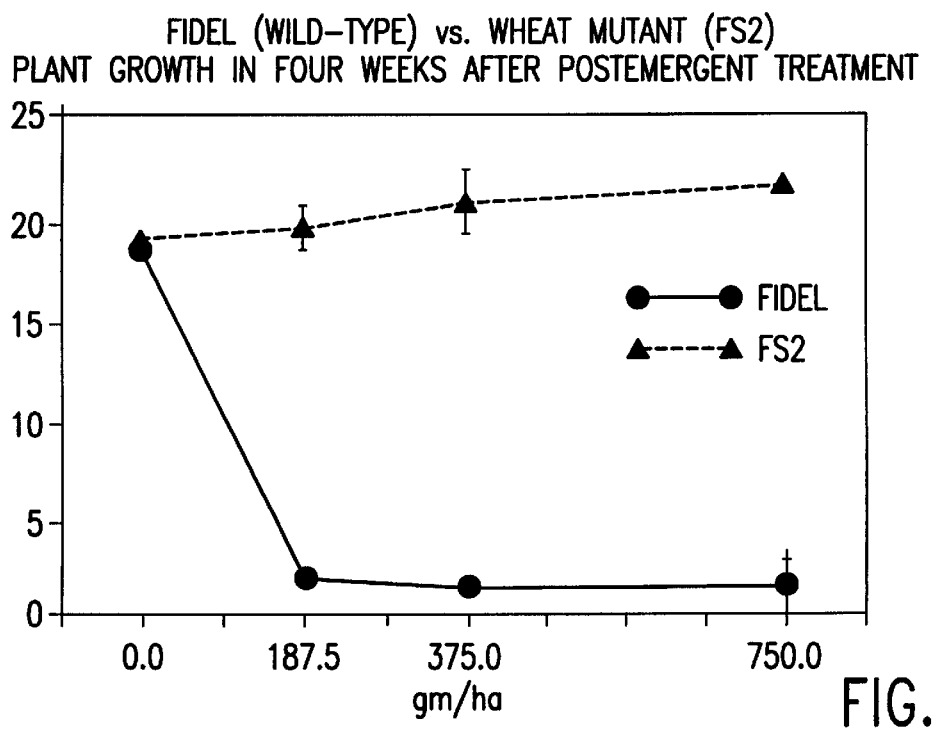
FIG. 26 depicts a comparison of plant growth (in cm.) of wild-type wheat (Fidel) versus the $F_2$ mutant from bulked $M_3$–$M_4$ seed four weeks after post-emergence treatment with an imidazolinone herbicide, Compound 7.

Cross-resistance to the sulfonylureas (FIGS. 21, 22 and 24), the sulfamoylurea (FIG. 23) or the sulfonylcarboxamide (FIG. 25) is 0–2 fold, similar to that observed in earlier studies with OUST™. The resistance to the imidazolinone Compound 7 is similar to that observed previously for PURSUIT™ or ARSENAL™ (greater than 10 fold) (FIG. 26). No appreciable increases in resistance to non-imidazolinone herbicides are observed.

EXAMPLE 4

Field trials

1. Field Trial I

A field study is conducted to evaluate the tolerance of the imidazolinone-resistant wheat selections, FS1–FS4, to postemergent applications of imidazolinone herbicides. The variety Fidel, from which these selections are derived, is included as a susceptible check. Because Fidel is a French winter wheat variety and unadapted to New Jersey, this test is intended to evaluate the relative effects of the herbicide treatments on grain yields rather than to measure actual yield potentials for the genotypes. Thus, yields are presented as grams/plot rather than bushels/acre or metric tons/ha.

$M_4$ bulked seed from parental lines, FS1, FS2, FS3 and FS4 and Fidel wild-type, is used in this field trial. The trial is planted in an incomplete split plot design with the main plot as herbicide-rate combination and the split plot as genotypes. There are three replicates for each treatment (chemical and rate), however replicates #2 and #3 do not include the mutant wheat selection FS3 due to lack of sufficient bulked seed. The plots are three meters long and 1.5 meters wide (7 rows with 7 inch spacing between rows) with approximately 25 seed planted per row. There is a one meter space between wheat lines and ten meters between replicates.

The treatments include the following:

| Untreated Controls | | |
|---|---|---|
| PURSUIT ™: | 100 and 200 | g/ha |
| Compound 2: | 50 and 100 | g/ha |
| Compound 8: | 100 and 200 | g/ha |

Compound 8 is 5-formyl-2-(4-isopropyl-4-methyl-5-oxo-2-imidazolin-2-yl)-nicotinic acid, 5-(dimethyl acetal), and is described in published European Patent Application Number 322,616.

Treatments are applied at a rate of 400 L/ha with a tractor mounted sprayer. Tween 20™ is used as a surfactant at 0.25% v/v. Wheat is treated at the Z22 stage or approximately 6 inches tall. Plant height and damage ratings are taken at 3 and 6 weeks after treatment. Yields are taken 10 weeks after treatment.

Figure 27:
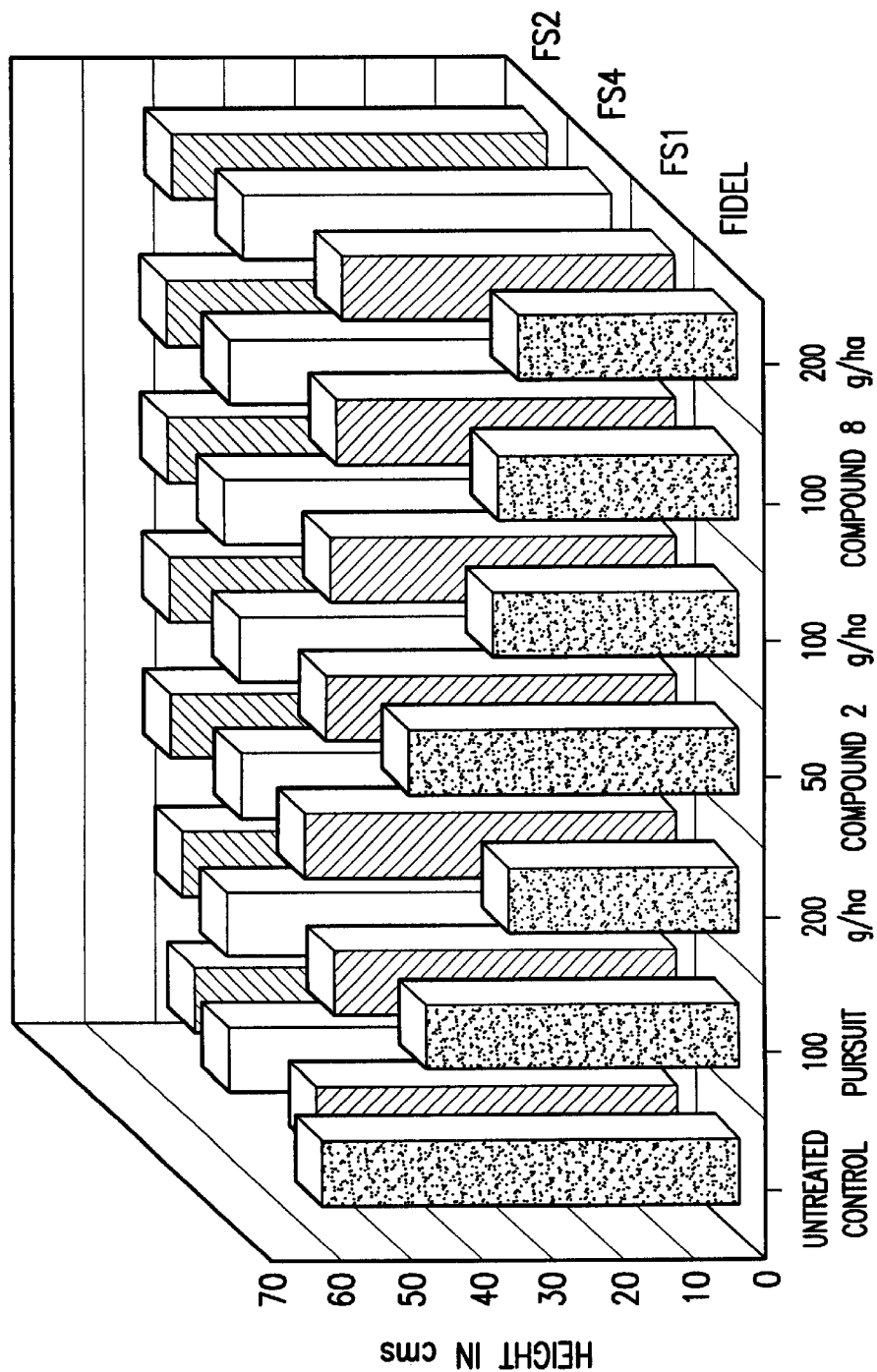
FIG. 27 depicts a comparison of plant height (in cm.) of wild-type wheat (Fidel) versus the $M_4$ wheat mutants from FS1, FS2 and FS4 three weeks after post-emergence treatment with PURSUIT™, Compound 2 or an imidazolinone herbicide, Compound 8.

Three weeks after treatment, the resistant wheat selections appear to be unaffected by these herbicide treatments as measured by plant height (FIG. 27). No obvious visible effects of the herbicide treatments on the resistant selections are observed. These selections when untreated are slightly shorter than untreated Fidel. The susceptible cultivar (Fidel) is severely stunted by these same treatments.

Figure 28:
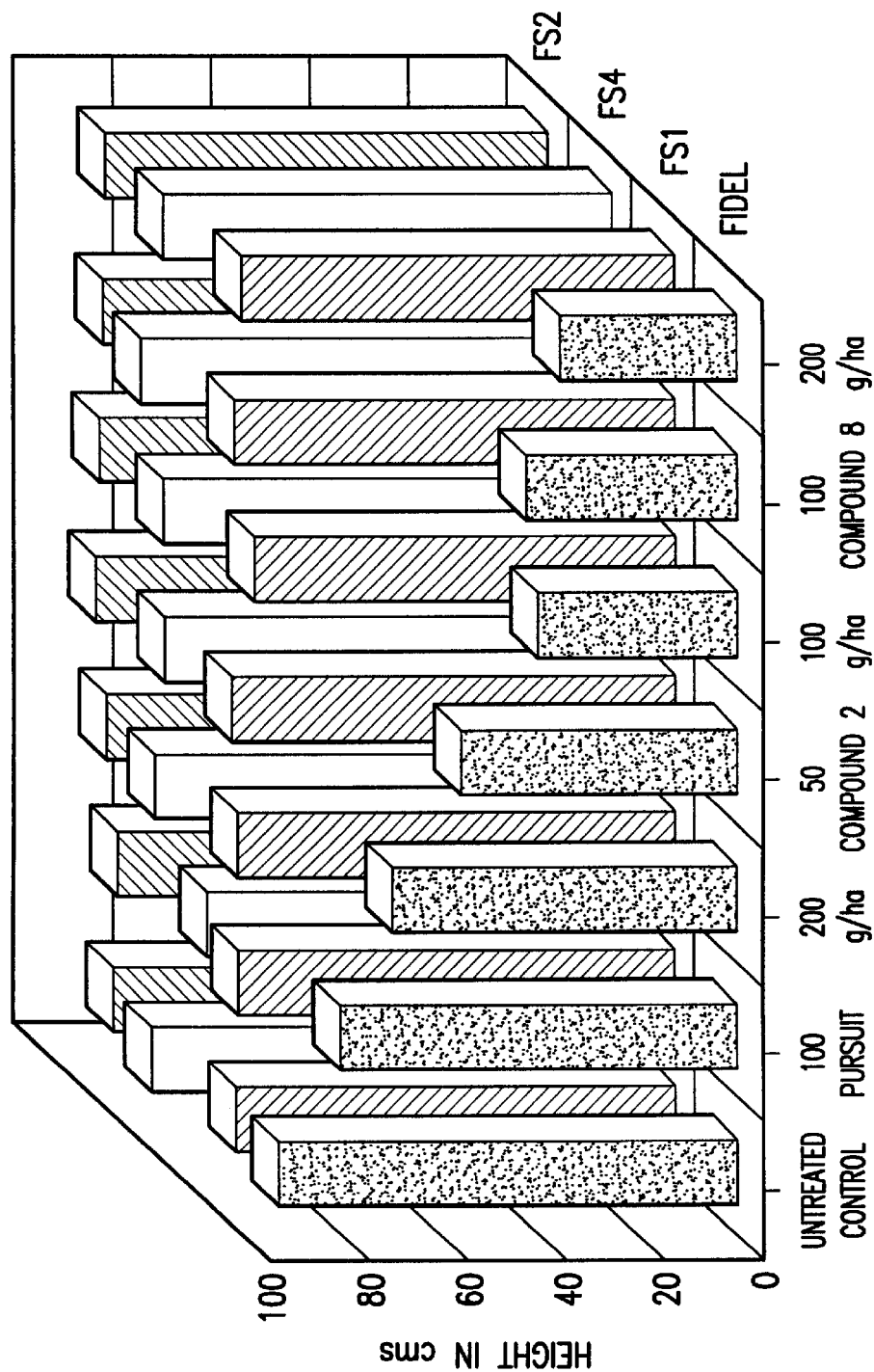
FIG. 28 depicts a comparison of plant height (in cm.) of wild-type wheat (Fidel) versus the $M_4$ wheat mutants from FS1, FS2 and FS4 six weeks after post-emergence treatment with PURSUIT™, Compound 2 or Compound 8.

The plant heights of the resistant wheat selections are still unaffected by herbicide treatment at six weeks after treatment (FIG. 28). Fidel is severely stunted or killed by the herbicide treatments while the resistant selections are apparently unaffected by the treatments. The final plant heights of the untreated selections are nearly equal to the height of untreated Fidel, even though at three weeks after treatment, the untreated selections are shorter than untreated Fidel. The resistant wheat selections appear to grow at a somewhat slower rate than unsprayed Fidel, presumably due to deleterious recessive mutations. These recessive mutations are removed by backcrossing using techniques available to those skilled in the art.

Figure 29:
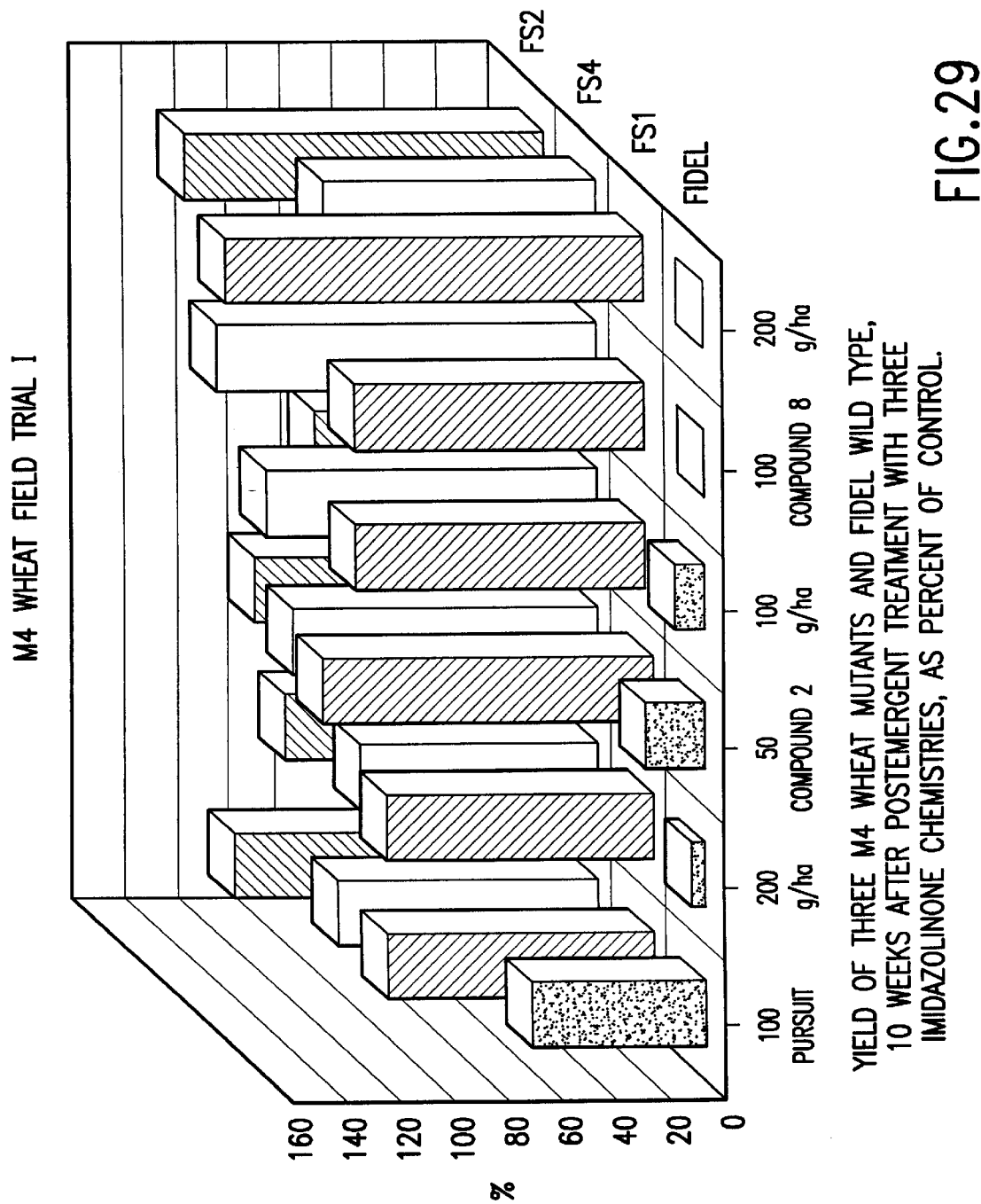
FIG. 29 depicts a comparison of the yield (as a percentage of control plants) of wild-type wheat (Fidel) versus the $M_4$ wheat mutants from FS1, FS2 and FS4 ten weeks after post-emergence treatment with PURSUIT™, Compound 2 or Compound 8.

FS1, FS2, and FS4 exhibit no yield reductions following postemergent treatment with any of the herbicide treatments. In contrast, Fidel has a 35% yield reduction when treated with PURSUIT™ at 100 g/ha and a greater than 75% yield reduction with the other herbicide treatments. The untreated Fidel yields significantly more than FS1 or FS4 (133 g/plot versus 40 g/plot and 76 g/plot, respectively). The mean yield for FS2 (98 g/plot) is also less than unsprayed Fidel, but not significantly less at ten weeks after treatment (FIG. 29). The lower yields of the selections are not unexpected; the mutants exhibit less vigor and weaker stand establishment than Fidel, presumably due to the presence of deleterious genes caused by the mutagenesis procedure but unrelated to the imidazolinone resistance trait. It is somewhat surprising that FS1, FS2, and FS4 display such wide differences in yield considering that all three are very likely derived from the same mutational event. The selections appear to be fully resistant to the herbicide treatments tested with respect to both plant height and grain yield.

2. Field Trial II

A second field study is planted to evaluate the tolerance of the imidazolinone resistant wheat selections, FS4, to postemergent applications of the imidazolinone herbicides PURSUIT™, CADRE™, Compound 2, and Compound 8, and the sulfonylurea herbicide, ACCENT™. CADRET™ is a registered trademark of American Cyanamid Company. CADRE™ is 2-(4-isopropyl-4-methyl-5-oxo-2-imidazolin-2-yl)-5-methylnicotinic acid and is described in U.S. Pat. No. 4,798,619. ACCENT™ is a registered trademark of E.I. du Pont de Nemours and Company and is 1-(4,6-dimethoxypyrimidin-2-yl)-3-(3-dimethylcarbamoyl-2-pyridylsulfonyl)urea. The variety Fidel is included as a susceptible check.

$M_5$ seeds from the highest yielding FS4 lines in the Field Trial I nursery are bulked and used in this field trial along with seed from Fidel. The trial is planted in an incomplete split plot design with the main plot representing herbicide treatment and the split plot representing genotypes. There are eleven treatments with three replicates for each treatment (chemical and rate). The plots are three meters long and 1.5 meters wide (7 rows with 7 inch spacing between rows) with a seeding density of approximately 100 seeds/m². There is a 0.5 meter space between wheat lines and three meters between replicates.

The treatments include the following:

| Untreated Controls | | |
|---|---|---|
| Imidazolinones: | | |
| PURSUIT ™: | 100 and 200 | g/ha |
| Compound 2: | 50 and 100 | g/ha |
| Compound 8: | 100 and 200 | g/ha |
| CADRE ™: | 50 and 100 | g/ha |
| Sulfonylurea: | | |
| ACCENT ™: | 20 and 40 | g/ha |

Treatments are applied at a rate of 200 L/ha with a backpack sprayer. X-77™, a non-ionic surfactant (Balent Corporation), is used as the wetting agent at 0.25% v/v. Wheat is treated at the Z27–Z28 stage when the plants are approximately 30–35 cm tall. Plant height and damage ratings are taken at 1, 2, 3 and 6 weeks after treatment. Yields are taken 10 weeks after treatment.

Figure 30:
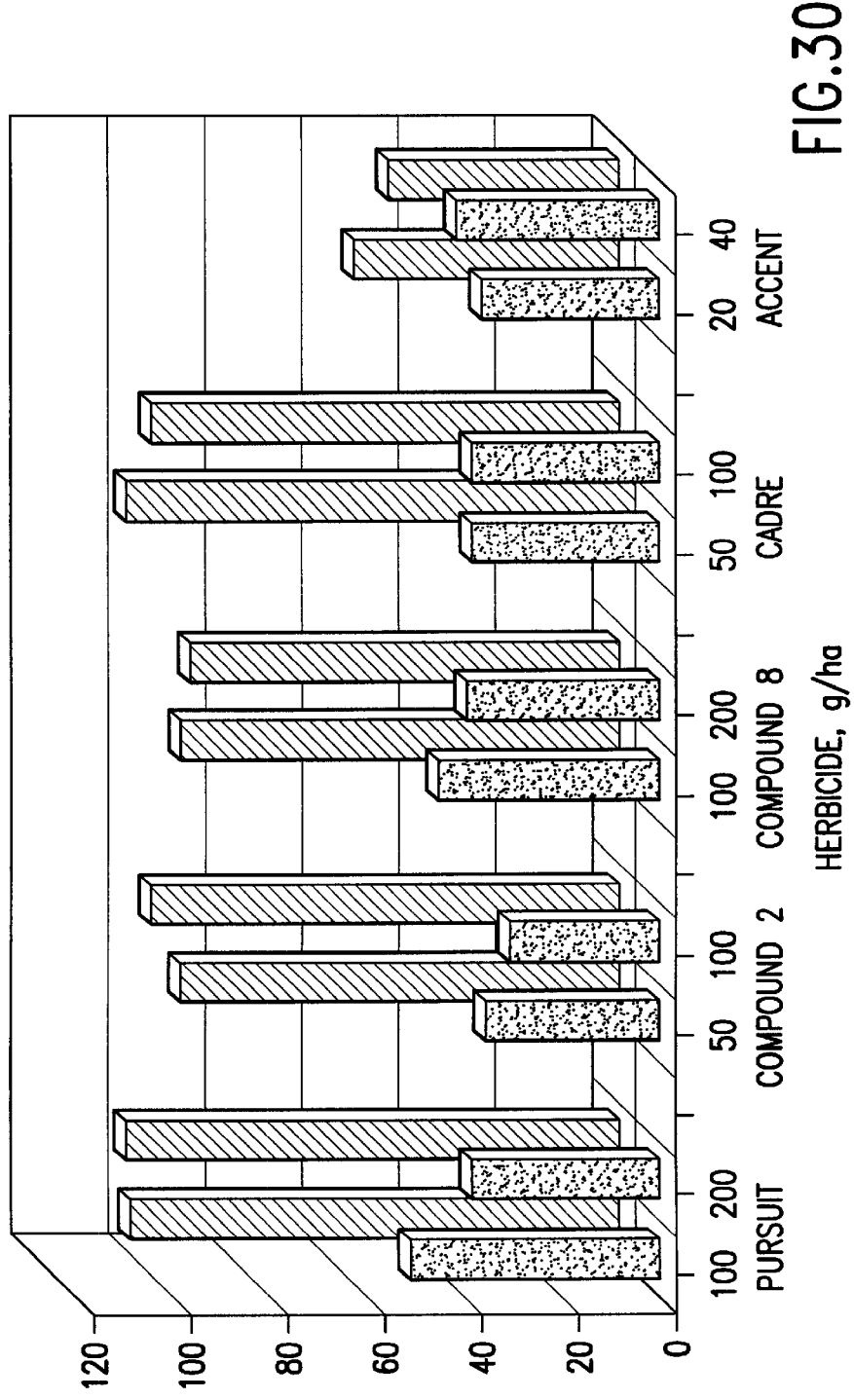
FIG. 30 depicts a comparison of growth (as a percentage of control plants) of wild-type wheat (Fidel) versus the $M_5$ wheat mutants from FS4 six weeks after post-emergence treatment with PURSUIT™, Compound 2, Compound 8, an imidazolinone herbicide, CADRE™, or a sulfonylurea herbicide, ACCENT™.
Figure 31:
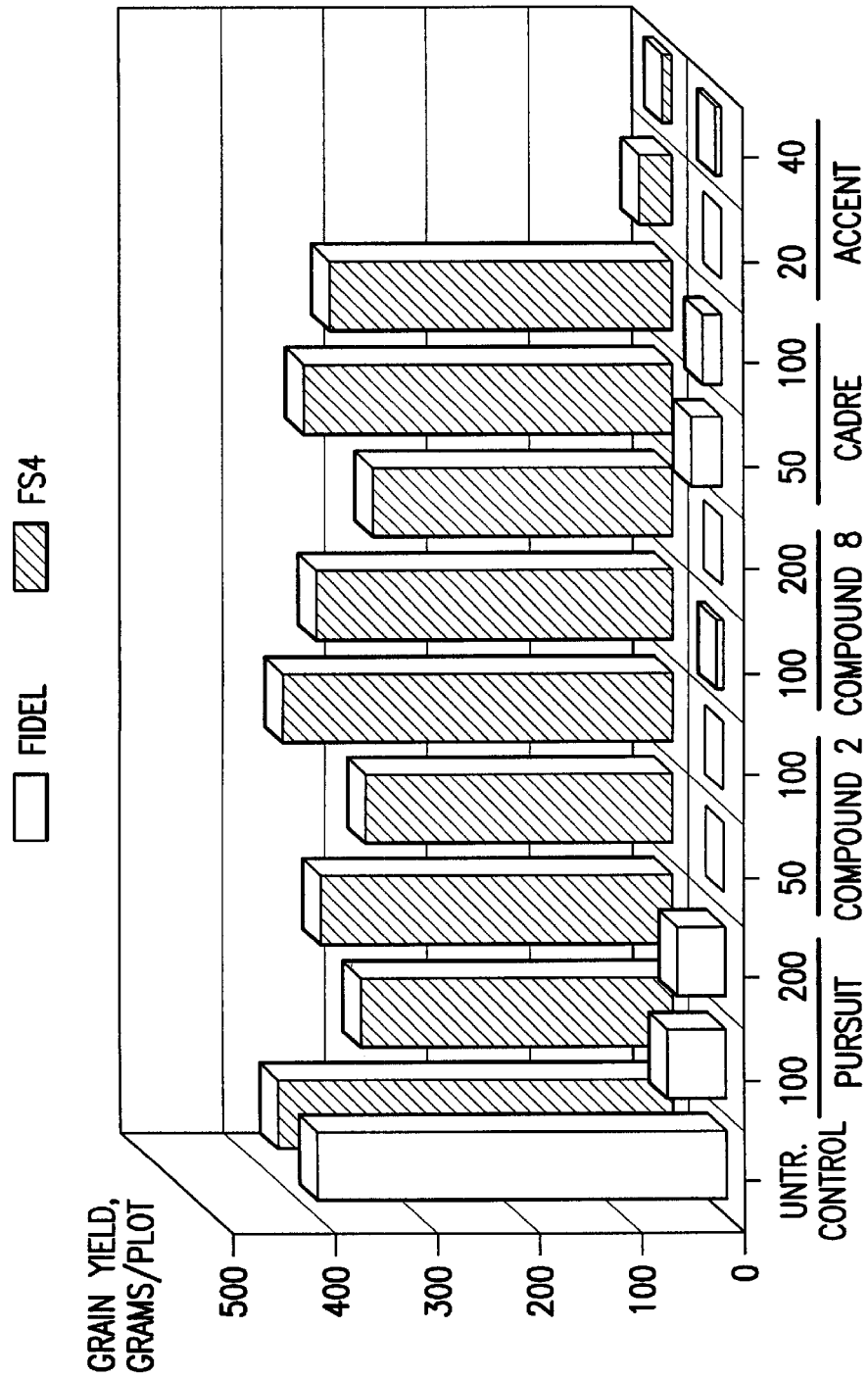
FIG. 31 depicts a comparison of the mean plot yield (in grams of grain per plot) of wild-type wheat (Fidel) versus the FS4 mutants ($M_5$ seeds) ten weeks after post-emergence treatment with PURSUIT™, Compound 2, Compound 8, CADRE™ or ACCENT™.
Figure 32:
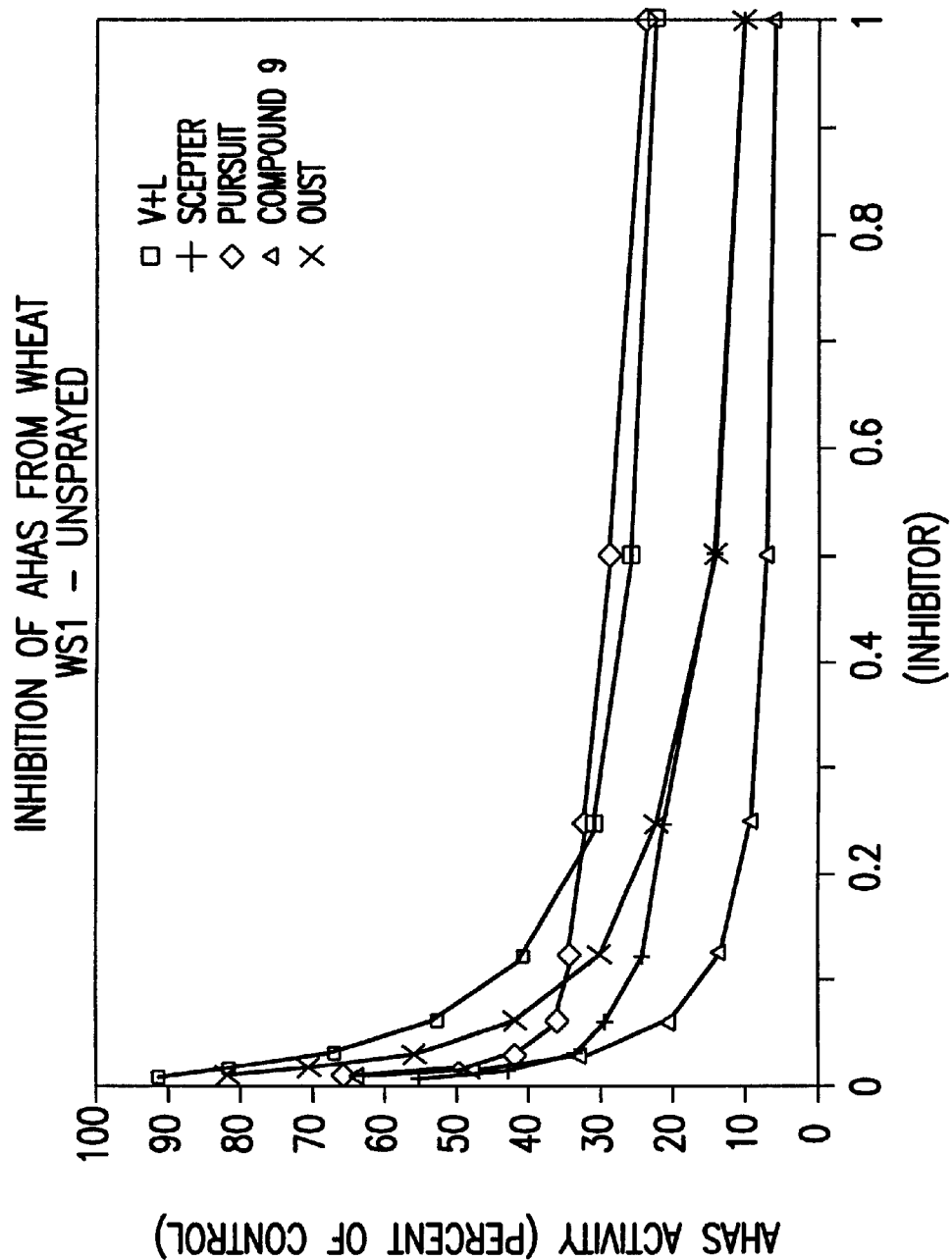
FIG. 32 depicts an in vitro enzyme assay which measures the inhibition of AHAS activity in FS1 mutant wheat (labelled WS1), not sprayed with herbicide after emergence, by valine and leucine (labelled V+L) as a control, SCEPTER™, PURSUIT™, Compound 9 and OUST™.
Figure 33:
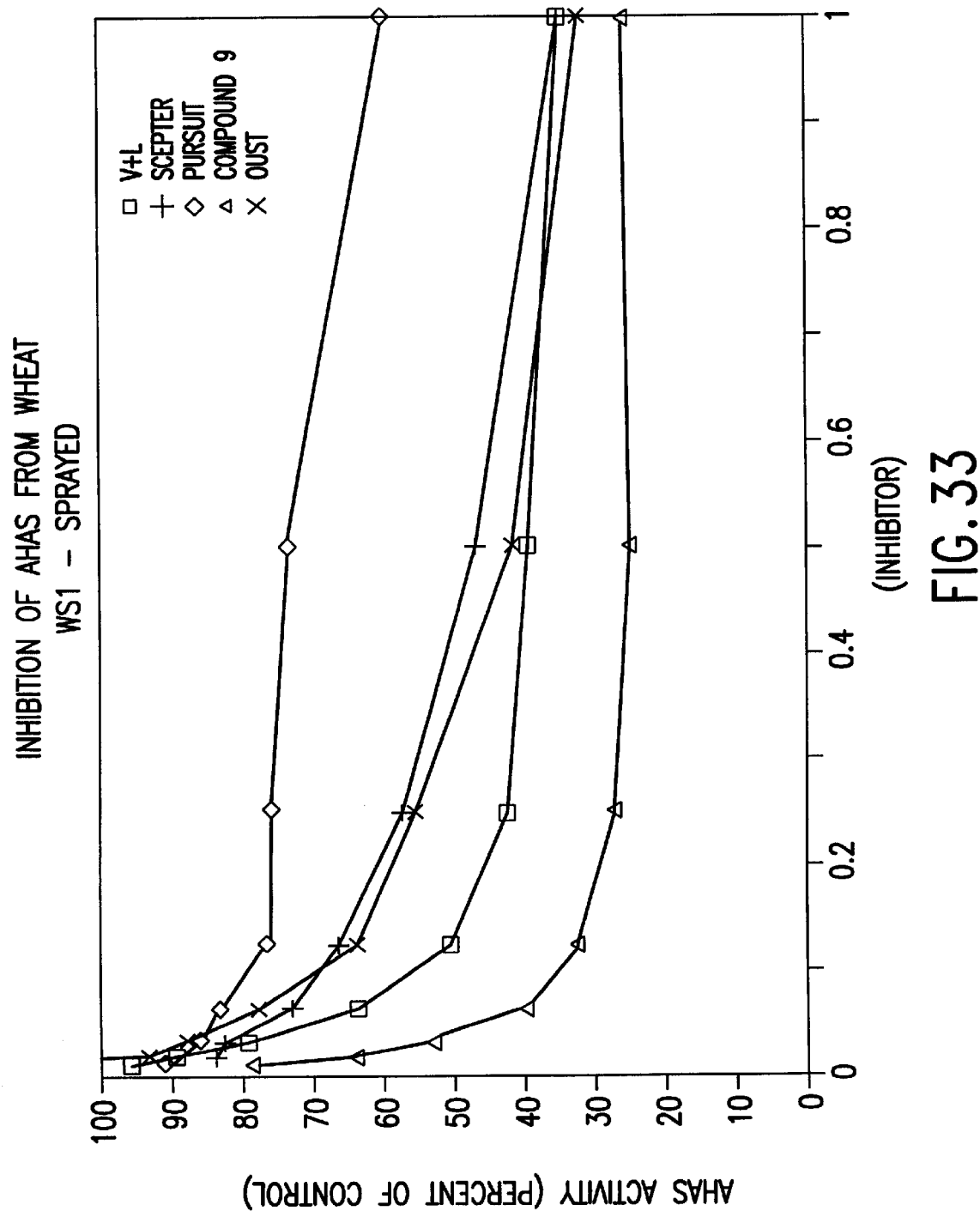
FIG. 33 depicts an in vitro enzyme assay which measures the inhibition of AHAS activity in FS1 mutant wheat (labelled WS1), sprayed with herbicide when the plants are three weeks old, by valine and leucine (labelled V+L) as a control, SCEPTER™, PURSUIT™, Compound 9 and OUST™.
Figure 34:
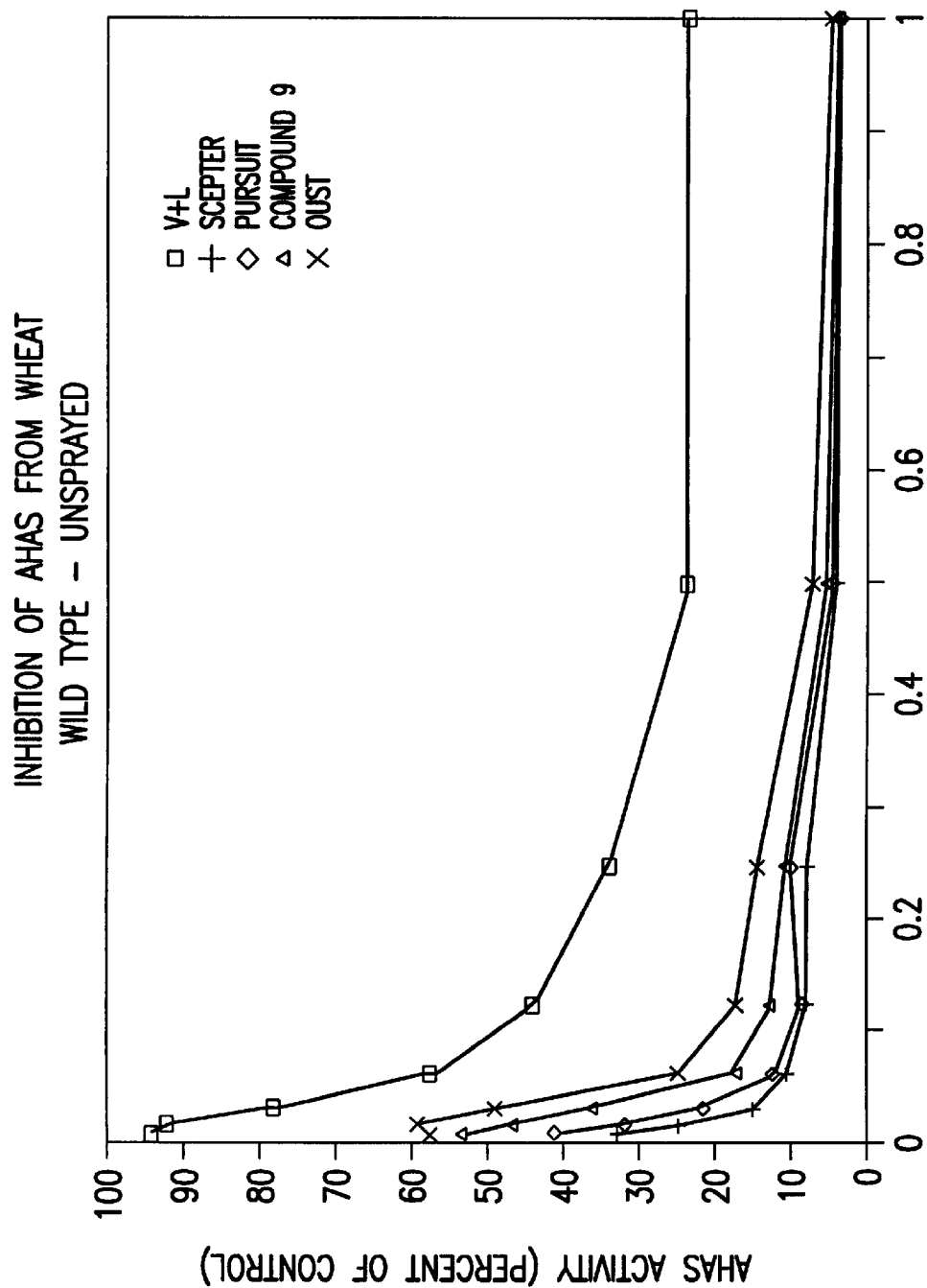
FIG. 34 depicts an in vitro enzyme assay which measures the inhibition of AHAS activity in wild type wheat (Fidel), not sprayed with herbicide after emergence, by valine and leucine (labelled V+L) as a control, SCEPTER™, PURSUIT™, Compound 9 and OUST™.
Figure 35:
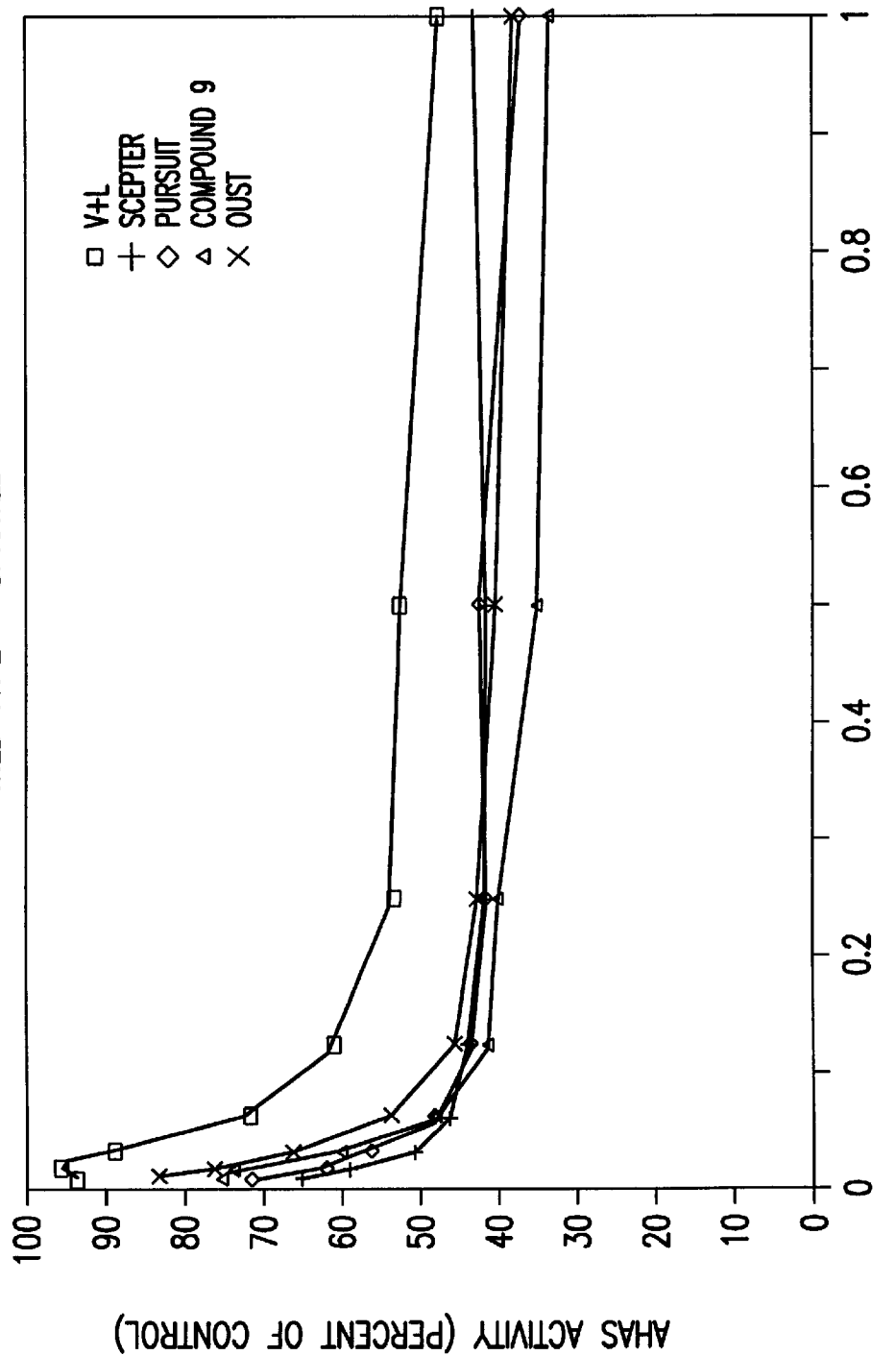
FIG. 35 depicts an in vitro enzyme assay which measures the inhibition of AHAS activity in wild type wheat (Fidel), sprayed with herbicide when the plants are three weeks old, by valine and leucine (labelled V+L) as a control, SCEPTER™, PURSUIT™, Compound 9 and OUST™.
Figure 36:
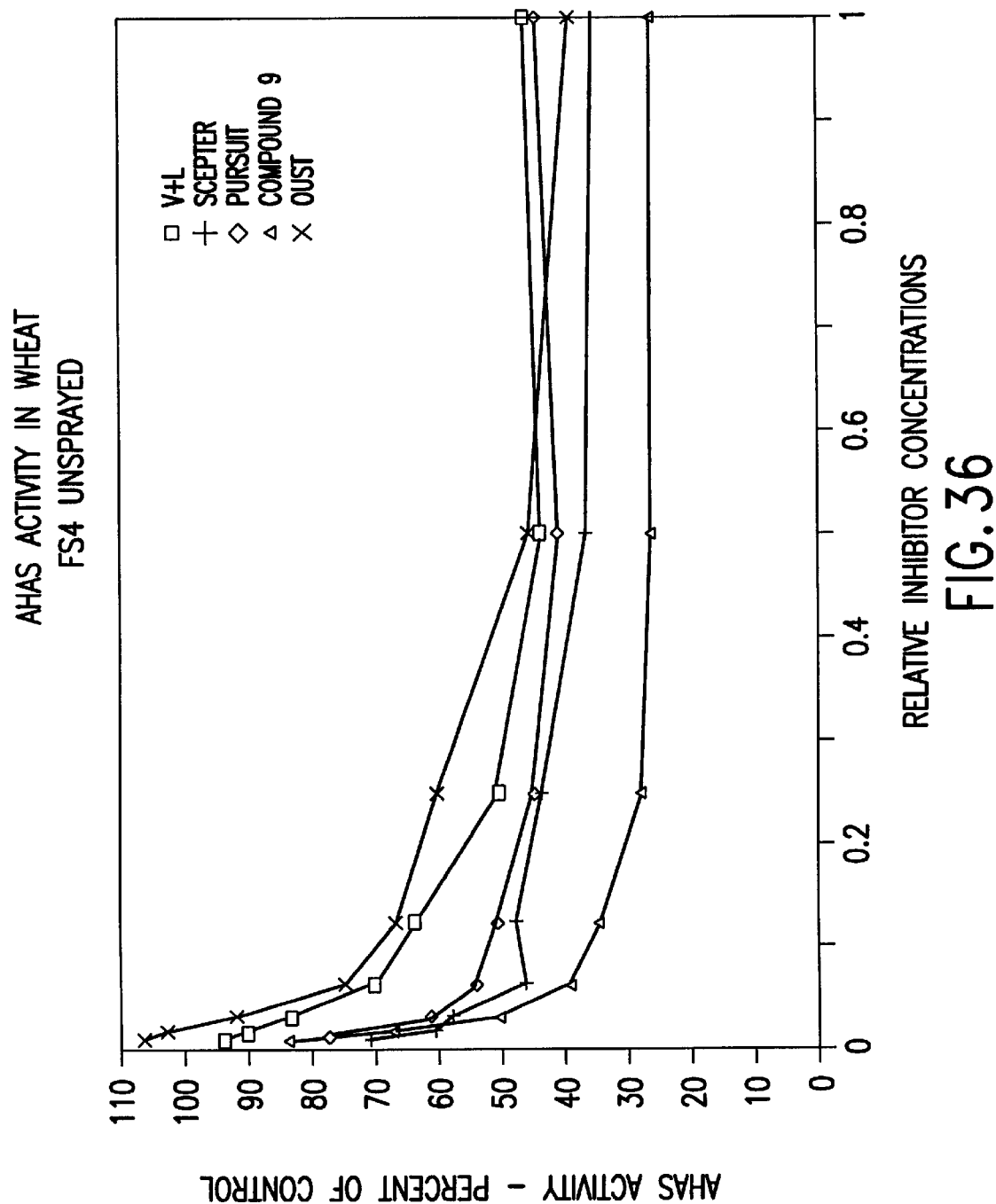
FIG. 36 depicts an in vitro enzyme assay which measures the inhibition of AHAS activity in FS4 mutant wheat, not sprayed with herbicide after emergence, by valine and leucine (labelled V+L) as a control, SCEPTER™, PURSUIT™, Compound 9 and OUST™.
Figure 37:
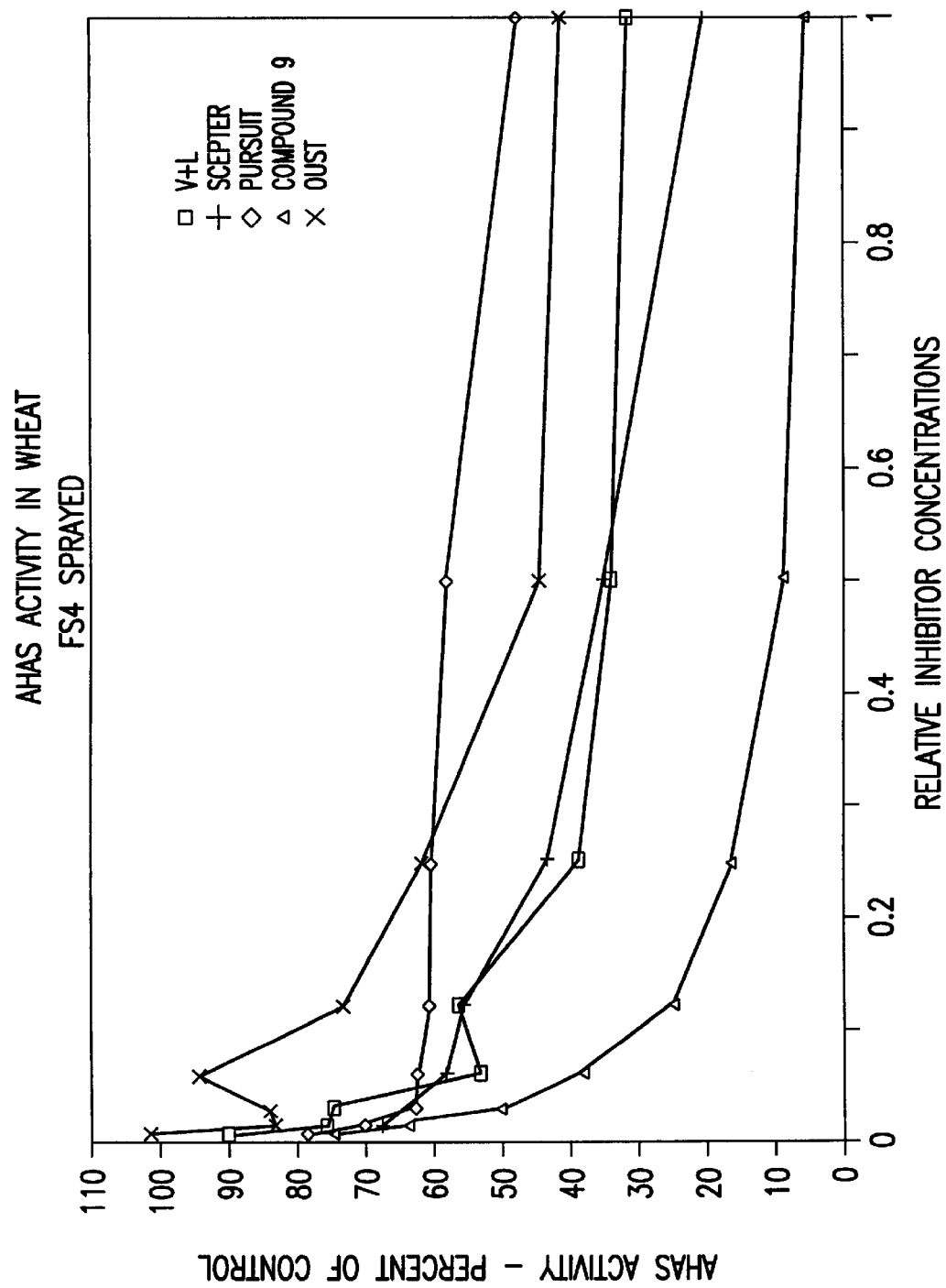
FIG. 37 depicts an in vitro enzyme assay which measures the inhibition of AHAS activity in FS4 mutant wheat, sprayed with herbicide when the plants are three weeks old, by valine and leucine (labelled V+L) as a control, SCEPTER™, PURSUIT™, Compound 9 and OUST™.
Figure 38:
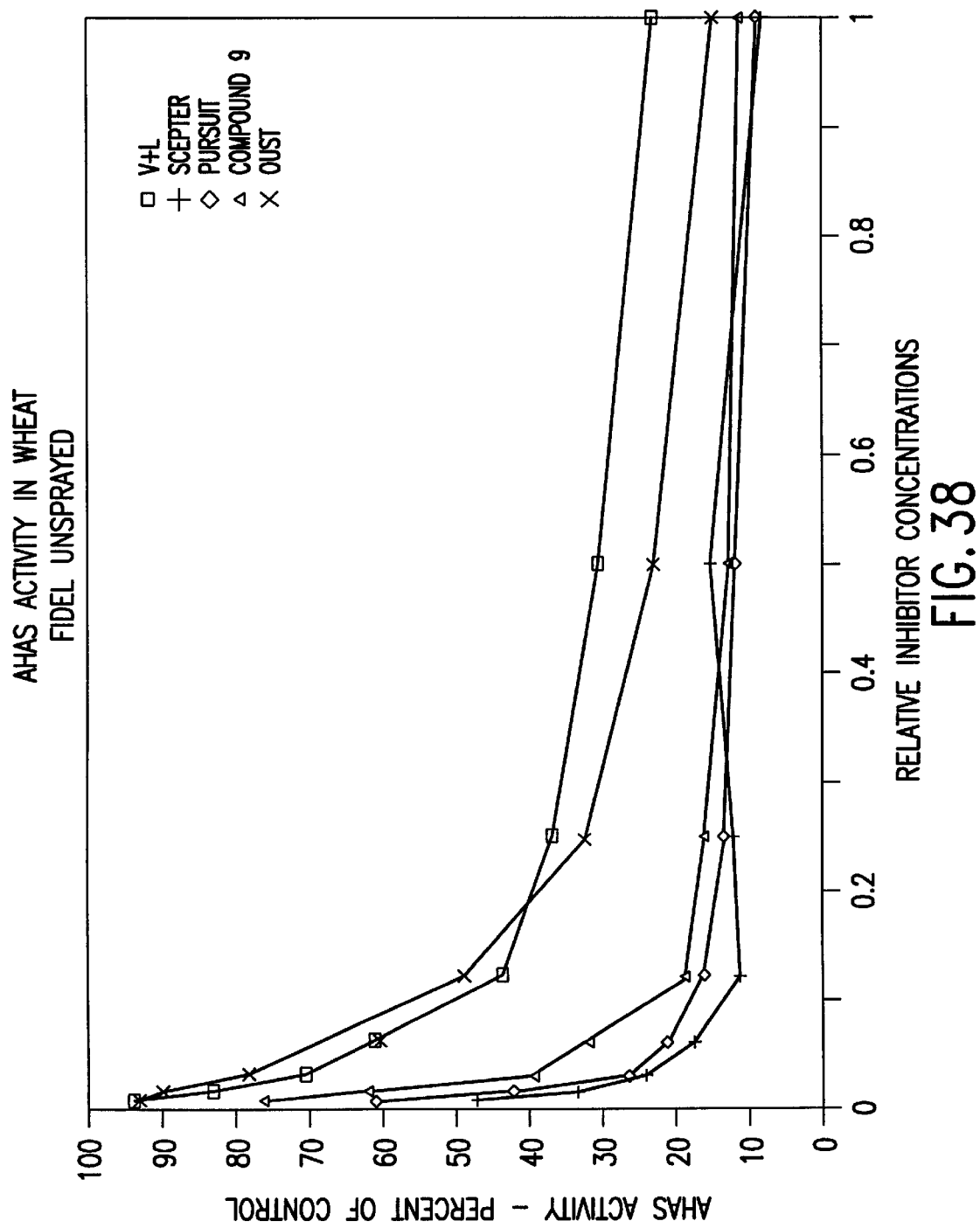
FIG. 38 depicts an in vitro enzyme assay which measures the inhibition of AHAS activity in wild type-wheat (Fidel), not sprayed with herbicide after emergence, by valine and leucine (labelled V+L) as a control, SCEPTER™, PURSUIT™, Compound 9 and OUST™.
Figure 39:
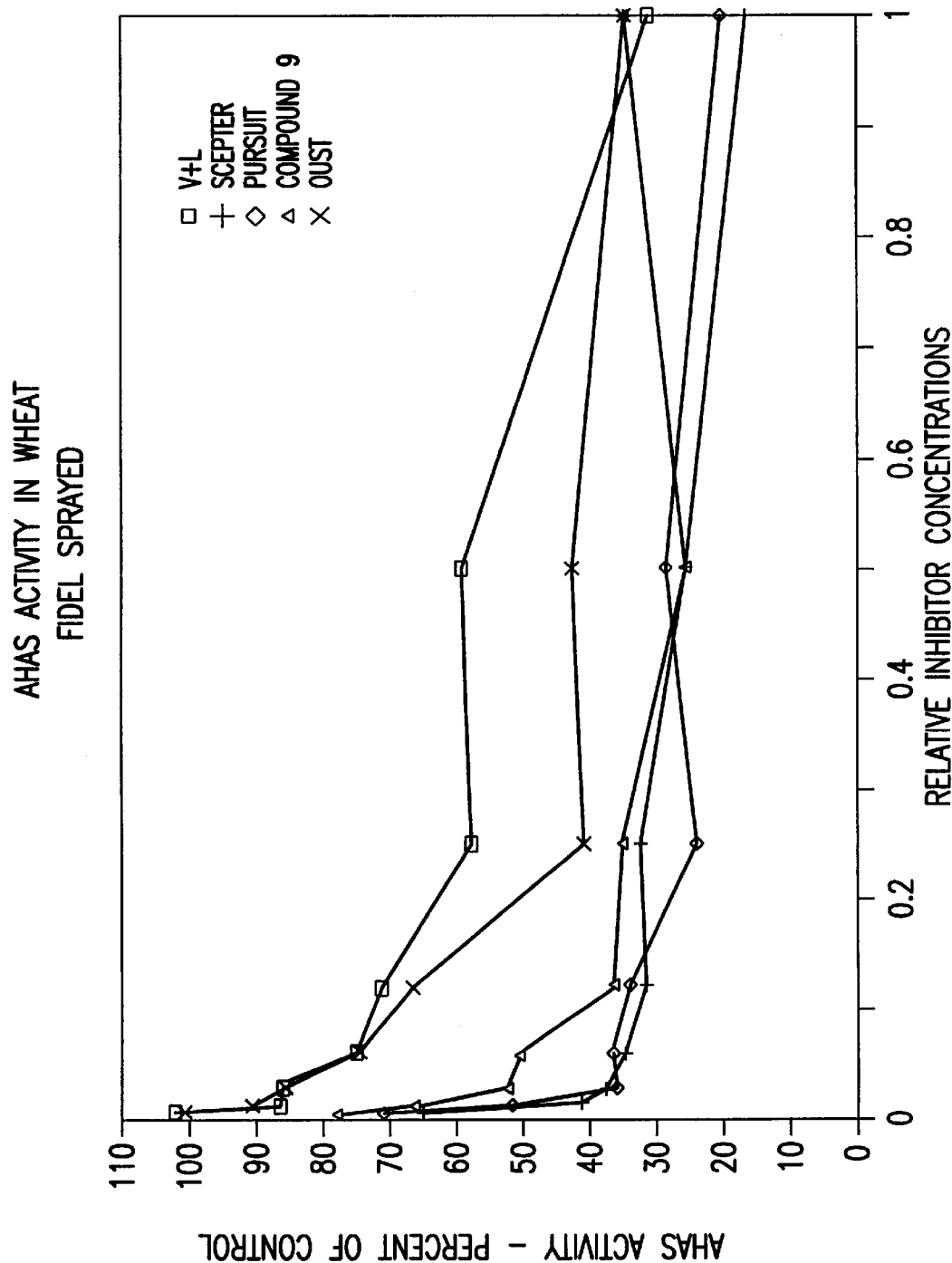
FIG. 39 depicts an in vitro enzyme assay which measures the inhibition of AHAS activity in wild type wheat (Fidel), sprayed with herbicide when the plants are three weeks old, by valine and leucine (labelled V+L) as a control, SCEPTER™, PURSUIT™, Compound 9 and OUST™.

After three weeks, Fidel growth is severely inhibited by all herbicide treatments. The resistant selection FS4 exhibits tolerance to all the imidazolinones tested; however, no cross resistance to the sulfonylurea herbicide (ACCENT™) is observed. FIG. 30 shows measurements taken at six weeks after treatment, indicating that there is no effect of postemergent treatment with PURSUIT™, CADRE™, Compound 2, or Compound 8 on final plant height. The resistant wheat has little or no tolerance to ACCENT™. The comparable susceptible variety is severely stunted or killed at these herbicide rates. Grain yields presented as the means across three replications are presented in FIG. 31. Grain yield of the resistant wheat selection FS4 is not reduced by any of the imidazolinone treatments. Yields of Fidel are severely reduced or eliminated by treatment with imidazolinone herbicides. Both the resistant and susceptible Fidel give little or no grain yield following treatment with ACCENT™. The effects on grain yield resulting from treatment of Fidel with imidazolinones are even more severe than the reductions in plant height described above.

The resistant wheat used to plant this field trial is obtained by bulking several seed increase plots harvested in Field Trial I. Each increase plot is derived from a single plant. Even though no backcrossing to Fidel is done with this material, seed sources with poor germination and agronomic performance are able to be eliminated. As a result, grain yields of the resistant selections are much improved as compared to those measured in Field Trial I. The yields obtained for resistant wheat in untreated control plots are equal to those obtained for susceptible Fidel in untreated plots. This indicates that the inclusion of a gene for imidazolinone-resistance has no inherent effect on grain yield.

EXAMPLE 5

Enzyme Studies

1. Initial Assay ($M_3$ Plants)

Herbicide Application: $M_3$ plants from the four initial mutant plants (FS1, FS2, FS3 and FS4), are tested for metabolic AHAS (acetohydroxyacid synthase) activity. Plants exhibiting resistance after the first seed soak and spray screen with PURSUIT™ are transferred from flats to individual pots. When these plants are three weeks old, two plants of each mutant selection, FS1–FS4, receive a second application of PURSUIT™ at 62.5 g/ha while two of each selection are left unsprayed. Sprayed and unsprayed susceptible Fidel plants are also included in this experiment. Approximately half the foliage above the soil line of each plant is removed and assayed two days after the herbicide application for inhibition of AHAS by valine and leucine (as a control), SCEPTER™, PURSUIT™, OUST™, and a sulfonylcarboxamide herbicide, Compound 9. Compound 9 is 2-acetamido-2,3-dimethyl-N-(p-tolylsulfonyl) butyramide, and is described in U.S. Pat. No. 4,883,914.

In unsprayed plants, weak resistance to PURSUIT™ is seen in the resistant wheat lines. However, a dramatic increase in the AHAS resistance to PURSUIT™ is seen in the sprayed FS1–FS4 plants as compared to the sprayed wild type. FIGS. 32–35 demonstrate these results for one of the four resistant selections (FS1) and for wild-type (susceptible) Fidel plants. Therefore, resistance of FS1–FS4 to PURSUIT™ appears to be due to the presence of an altered AHAS which is resistant to inhibition by PURSUIT™.

Enzyme Extraction: For the extraction of AHAS, 10 grams of tissue are powdered in liquid nitrogen and then homogenized in 100 mM potassium phosphate buffer (pH 7.5) containing 10 mM pyruvate, 5 mM $MgCl_2$, 5 uM EDTA, 100 uM FAD, 1 mM valine, 1 mM leucine, 10% glycerol, and 10 mM cysteine. The homogenate is filtered through a nylon cloth (53 uM mesh) and centrifuged at 25,000 g for 20 minutes. The supernatant fraction is brought to 50% saturation with respect to $(NH_4)_2SO_4$ and allowed to stand for 20–30 minutes on ice. It is then centrifuged at 25,000 g for 20 minutes and the supernatant is discarded. The ammonium sulfate pellet is dissolved in 50 mM potassium phosphate buffer (pH 7.5) containing 1 mM EDTA and 100 mM NaCl and used for the assay procedures.

AHAS Assay: AHAS activity is measured by estimation of the product, acetolactate, after conversion by decarboxylation in the presence of acid to acetoin. Standard reaction mixtures contain the enzyme in 50 mM potassium phosphate buffer (pH 7.0) containing 100 mM sodium pyruvate, 10 mM $MgCl_2$, 1 mM thiamine pyrophosphate, and 10 uM FAD. This mixture is incubated at 37° C. for one hour after which time the reaction is stopped with the addition of $H_2SO_4$ to make a final concentration of 0.85% $H_2SO_4$ in the tube. The reaction product is allowed to decarboxylate at 60° C. for 15 minutes. The acetoin formed is determined by incubating with creatine (0.17%) and 1-napthol (1.7% in 4N NaOH) by the method of Westerfield (Westerfield, W. W., *J. Biol. Chem.*, 161, 495–502 (1945)). Maximum color is observed by incubation at 60° C. for 15 minutes and then further incubation at room temperature for 15 minutes. The absorption of color complex is measured at 520 nm. Appropriate checks of direct acetoin formation during the enzyme assay are made. Each assay is run at least in duplicate and the experiments are repeated a minimum of two times.

2. Enzyme Assay I ($M_4$ Plants)

Herbicide Application: Two flats are planted with approximately 100 seeds of each wheat selection (FS1, FS2, and FS4) and Fidel in sterile Metro Mix 350. Ten days later, each flat is sprayed postemergence with 62.5 g/ha of PURSUIT™. The spray delivery rate is 400 L/ha with a belt speed of 8.2 sec/rev using nozzle #65015E. Tween 20™ is used as a surfactant at 0.25% v/v. The plants are harvested three days later and assayed for AHAS activity.

Enzyme Extraction and AHAS Assay: As previously described.

3. Enzyme Assay II ($M_4$ Plants)

Herbicide Application: As described above (Enzyme Assay I) except that the spray delivery rate is 950 l/ha with a belt speed of 12.8 sec/rev using nozzle #40015E.

Enzyme Extraction and AHAS Assay: As previously described.

The results from these two sets of experiments are very similar. AHAS activity from all four homozygous resistant mutant lines obtained from unsprayed plants shows moderate levels of resistance to PURSUIT™ as compared to the enzyme from the wild type control plants (Fidel). However, a significantly higher level of resistance to PURSUIT™ is observed in the enzyme from selections which are sprayed as compared to the enzyme from the sprayed Fidel plants (FIGS. 36–39). Some resistance to SCEPTER™ and OUST™ is also observed, but the level of resistance is lower than that for PURSUIT™. The spectrum and level of resistance to various herbicides is very similar in all the mutants which suggests that all four mutants may be the result of a single mutational event. This conclusion is confirmed by genetic approaches described above.

What is claimed is:

1. A method of screening for the selection of mutations which confer acetohydroxyacid synthase inhibiting herbicide resistance to wheat which comprises mutagenizing wheat seeds with a chemical mutagen, soaking the mutagenized seeds in an acetohydroxyacid synthase inhibiting herbicide-containing solution containing a particular class of acetohydroxyacid synthase inhibiting herbicide, planting the soaked seeds in soil and spraying the soil containing seeds with an acetohydroxyacid synthase inhibiting herbicide of the same class as that used in the seed soak step prior to the emergence of seedlings from the soil, such that the emergent wheat plants which are normal in appearance are resistant to the class of acetohydroxyacid synthase inhibiting herbicide used in the seed soak and spraying steps.

2. The method of claim 1 wherein the chemical mutagen is selected from the group consisting of sodium azide, N-methyl-N-nitrosourea, N-ethyl-N-nitrosourea, ethyl methanesulfonate, hydroxylamine and hydrazine.

3. The method of claim 2 wherein the chemical mutagen is sodium azide.

4. The method of claim 1 wherein the acetohydroxyacid synthase inhibiting herbicide used in the seed soak step is the same as that used in the seed spraying step.

5. The method of claim 1 wherein the acetohydroxyacid synthase inhibiting herbicide used in the seed soak step is different from that used in the seed spraying step.

6. The method of claim 1 wherein the class of acetohydroxyacid synthase inhibiting herbicide is selected from the group consisting of the imidazolinones, the sulfamoylureas, the sulfonylcarboxamides, the sulfonamides and the sulfonylureas.

7. The method of claim 6 wherein the class of acetohydroxyacid synthase inhibiting herbicide is the imidazolinones.

8. The method of claim 7 wherein the imidazolinone is selected from the group consisting of 2-(4-isopropyl-4-methyl-5-oxo-2-imidazolin-2-yl)-nicotinic acid, 2-(4-isopropyl-4-methyl-5-oxo-2-imidazolin-2-yl)-3-quinolinecarboxylic acid, 5-ethyl-2-(4-isopropyl-4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, 5-formyl-2-(4-isopropyl-4-methyl-5-oxo-2-imidazolin-2-yl)-nicotinic acid, 5-(dimethyl acetal), 3-(4-isopropyl-4-methyl-5-oxo-2-imidazolin-2-yl)-2-methylcrotonic acid), 2-(4-isopropyl-4-methyl-5-oxo-2-imidazolin-2-yl)-5-methylnicotinic acid, and a mixture of methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate.

9. The method of claim 8 wherein the imidazolinone is selected from the group consisting of 5-ethyl-2-(4-isopropyl-4-methyl-5-oxo-2-imidazolin-2-yl)-nicotinic acid and 2-(4-isopropyl-4-methyl-5-oxo-2-imidiazolin-2-yl)-nicotinic acid.

10. The method of claim 9 wherein the imidazolinone is 5-ethyl-2-(4-isopropyl-4-methyl-5-oxo-2-imidazolin-2-yl)-nicotinic acid.

11. A method of screening for the selection of mutations which confer acetohydroxyacid synthase inhibiting herbicide resistance to wheat which comprises mutagenizing wheat seeds with a chemical mutagen, soaking the mutagenized seeds in an acetohydroxyacid synthase inhibiting herbicide-containing solution containing a particular class of acetohydroxyacid synthase inhibiting herbicide, planting the soaked seeds in soil and spraying the soil containing seeds with an acetohydroxyacid synthase inhibiting herbicide of a different class than that used in the seed soak step prior to the emergence of seedlings from the soil, such that the emergent wheat plants which are normal in appearance are resistant to both classes of acetohydroxyacid synthase inhibiting herbicides used in the seed soak and spraying steps.

* * * * *